United States Patent
Chi et al.

(10) Patent No.: US 8,557,988 B2
(45) Date of Patent: Oct. 15, 2013

(54) EMISSIVE TRANSITION-METAL COMPLEXES WITH BOTH CARBON-PHOSPHORUS ANCILLARY AND CHROMOPHORIC CHELATES, SYNTHETIC METHOD OF PREPARING THE SAME AND PHOSPHORESCENT ORGANIC LIGHT EMITTING DIODE THEREOF

(75) Inventors: Yun Chi, Hsinchu (TW); Jui-Yi Hung, Hsinchu (TW); Cheng-Huei Lin, Hsinchu (TW); Pi-Tai Chou, Taipei (TW); I-Hsuan Pai, Hsinchu (TW); Chien-Wei Hsu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/602,672

(22) Filed: Sep. 4, 2012

(65) Prior Publication Data

US 2013/0005975 A1    Jan. 3, 2013

Related U.S. Application Data

(60) Division of application No. 12/385,864, filed on Apr. 22, 2009, now Pat. No. 8,288,543, which is a continuation-in-part of application No. 12/000,035, filed on Dec. 7, 2007, now Pat. No. 8,030,490.

(60) Provisional application No. 60/877,603, filed on Dec. 29, 2006.

(51) Int. Cl.
C07F 15/00    (2006.01)
C07F 3/12    (2006.01)

(52) U.S. Cl.
USPC ............... 546/4; 546/10; 548/103; 548/108; 544/225; 428/690

(58) Field of Classification Search
None
See application file for complete search history.

(56) References Cited

U.S. PATENT DOCUMENTS 7,759,490 B2    7/2010    Tao et al.
2007/0001166 A1    1/2007    Tao et al.

FOREIGN PATENT DOCUMENTS

JP    2008-10647        1/2008
JP    2008-239565 A    10/2008

OTHER PUBLICATIONS

Doherty et al., Organometallics (2003), 22, pp. 1452-1462.*
Shiu et al. Journal of Organometallic Chemistry 650(2002) 268-273.*
Moorlag et al., "Switchable thiophene coordination in Ru(II) bipyridyl phosphinoterthiophene complexes", Chem. Comm., 2002, vol. 24, pp. 328-329.
Moorlag et al., Chemical Communications, 2003, vol. 1, p. 166.
Moorlag et al., "Reversible Molecular Switching of Ruthenium Bis(bipyridyl) Groups Bonded to Oligothiophenes: Effect on Electrochemical and Spectroscopic Properties", J. Am. Chem. Soc., 2005, vol. 127, pp. 6382-6393.
Moorlag et al., "Conjugation Length Dependent Ground and Excited State Electronic Behavior in Oligothienyl Ru Complexes", Inorganic Chemistry, vol. 45, No. 18, pp. 7044-0746.

* cited by examiner

*Primary Examiner* — Nyeemah A Grazier
(74) *Attorney, Agent, or Firm* — Bacon & Thomas, PLLC

(57) ABSTRACT

The present invention provides a phosphorescent tris-chelated transition metal complex having one carbon-nitrogen (C^N) or nitrogen-nitrogen (N^N) chromophoric ligand forming a coordination sphere thereof with a transition metal, and two identical carbon-phosphorus (C^P) chelates being incorporated into the coordination sphere, wherein the metal is iridium, platinum, osmium or ruthenium, and the chromophoric ligands possess a relatively lower energy gap in comparison with that of the non-chromophoric chelate, the latter afforded an effective barrier for inhibiting the ligand-to-ligand charge transfer process, so that bright phosphorescence can be observed. The architecture and energy gap of the present molecular designs are suitable for generation of high efficiency blue, green and even red emissions.

21 Claims, 8 Drawing Sheets

EMISSIVE TRANSITION-METAL COMPLEXES WITH BOTH CARBON-PHOSPHORUS ANCILLARY AND CHROMOPHORIC CHELATES, SYNTHETIC METHOD OF PREPARING THE SAME AND PHOSPHORESCENT ORGANIC LIGHT EMITTING DIODE THEREOF

CROSS REFERENCE TO RELATED APPLICATIONS

This application is a divisional application of U.S. patent application Ser. No. 12/385,864, filed Apr. 22, 2009 now U.S. Pat. No. 8,288,543. The parent application is a continuation-in-part of U.S. patent application Ser. No. 12/000,035, filed Dec. 7, 2007, now U.S. Pat. No. 8,030,490 B2, which claims the benefit of U.S. Provisional Patent Application No. 60/877,603, filed on Dec. 29, 2006. The disclosures of U.S. patent application Ser. No. 12/385,864, U.S. Pat. No. 8,030,490 B2, and U.S. Provisional Patent Application No. 60/877,603 are incorporated herein by reference.

FIELD OF THE INVENTION

The present invention relates to iridium complexes, and more particularly to the phosphorescent iridium complexes with both carbon-phosphorus ancillary chelate(s) and chromophoric ligand(s), synthetic method of preparing the same and phosphorescent organic light emitting diode thereof.

BACKGROUND OF THE INVENTION

Phosphorescent organic light emitting diodes (OLEDs) are under intensive investigation because of their potential of achieving improved device brightness and performances. In contrast to the fluorescent emission, the electrophosphorescence of heavy transition-metal complexes are easily generated from both singlet and triplet excited states and, thus, the internal quantum efficiency can reach a theoretical level of unity, rather than the 25% inherent upper limit imposed by the formation of singlet excitons for the respective fluorescent counterparts. Thus, a great deal of effort has been spent on the second and third-row transition metal complexes, for developing highly efficient phosphors that can emit all three primary colors.

US 2008-0161568 A1 discloses a phosphorescent tris-chelated transition metal complex comprising i) two identical non-conjugated cyclometalated ligands being incorporated into a coordination sphere thereof with a transition metal, and one ligated chromophore being incorporated into the coordination sphere; or ii) one non-conjugated cyclometalated ligand forming a coordination sphere thereof with a transition metal, and two ligated chromophores being incorporated into the coordination sphere, wherein the metal is iridium, platinum, osmium or ruthenium, and the ligated chromophore possesses a relatively lower energy gap in comparison with that of the non-conjugated cyclometalated ligand, the latter afforded an effective barrier for inhibiting the ligand-to-ligand charge transfer process, so that a subsequent radiative decay from an excited state of these transition complexes will be confined to the ligated chromophore. The architecture and energy gap of the ligated chromophore are suitable for generation of high efficiency blue, green and even red emissions.

SUMMARY OF THE INVENTION

The present invention provides the phosphorescent metal complexes with both carbon-phosphorus (C^P) ancillary chelate(s) and chromophoric ligand(s), synthetic method of preparing the same and phosphorescent organic light emitting diode thereof for blocking the occurrence of unwanted ligand-to-ligand charge transfer (LLCT) processes and possibly, giving an enhanced quantum yield for emission across the whole visible spectral region. Definition of chromophoric ligands follows that of the traditional concepts, namely: a chromophoric ligand is part of a metal chelate responsible for its visible color and/or respective emission. Moreover, when a metal complex with at least one chromophoric ligand absorbs certain kind of energy from light source or electrical power supply, thus energy can be converted by exciting an electron from its ground state into an excited state, for which the frontier orbitals are principally localized in the region of chromophoric ligand(s) of the phosphorescent metal complexes. Typical chromophoric ligands comprise of aromatic, polyaromatic, or heterocyclic molecules that possess extensive π-conjugation over the whole chelating ligand.

The chromophoric ligands utilized in the present study can be classified to two kinds. The first class is denoted as (C^N)H, which comprise a nitrogen donor segment such as pyridine, isoqunioline and quinazoline as well as an aromatic or functionalized aromatic moiety that can react with the metal reagent via direct C—H activation, giving the so-called cyclometalated chelates. The second class is subsequently named as (N^N)H chelate, which possesses the neutral N-donor segment plus a second fragment with a N—H functional group, the latter can react with central metal ion in a fashion similar to the C—H activation occurred for the (C^N)H chelate, giving formation of an anionic (N^N) chelate interaction. Examples of these chromophoric ligands upon coordination to the metal center are listed below:

(C^N)H chelates

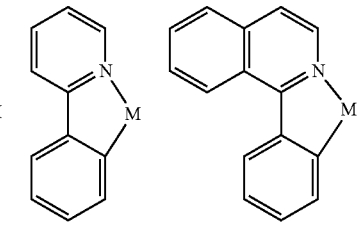

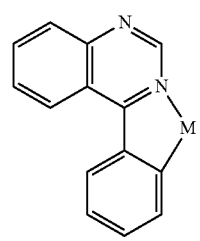

(N^N)H chelates

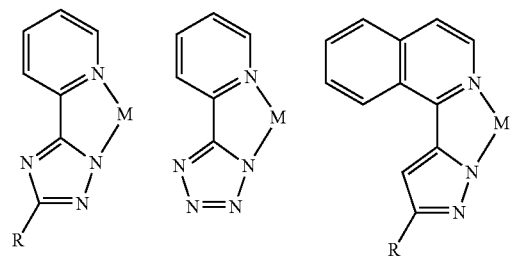

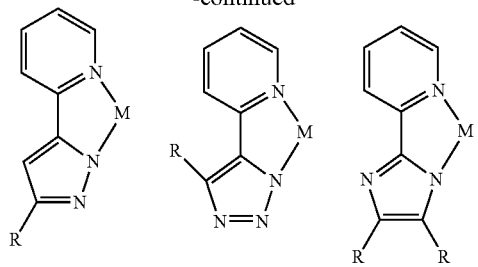

On the other hand, the carbon-phosphorus (C^P) chelate mentioned in the present invention can serve as "electronic blocker" due to the saturated nature of phosphine fragment and thus, represents another class of "non-conjugated" ancillary chelate. It is notable that both the covalent metal-carbon σ-interaction of the cyclometalated fragment and the π-accepting character of phosphine donor is expected to strengthen the metal-chelate bonding interaction and destabilizing the metal-centered dd excited states. Population of metal-centered dd excited states will be accompanied by elongation and severe distortion of metal-ligand bonds, promoting non-radiative decay to the ground state at the isoenergetic crossing point of the potential energy surfaces. Even if emissive excited states of different character, such as MLCT or ligand-centered ππ* states, lie at lower energies than the dd states, the latter can still exert a deleterious influence if they are thermally accessible. Thus, after lifting the dd excited state, the resulting metal complexes are expected to exhibit enhanced chemical stabilities, more balanced electrochemical and enhanced emission efficiency at room temperature. Beside, the saturated bonding nature of phosphine donor would discourage the orbital overlap between metal d-orbitals and the π-system of the carbon-phosphorus (C^P) chelate, and confine the electronic transitions occurred only at other chromophoric chelates. As anticipated, bright phosphorescence across the whole visible spectrum can be achieved through simple switch of the chromophoric ligands based on a facile synthetic approach documented in literature.

Several carbon-phosphorus ancillary chelate with abbreviation (C^P)H is indicated below:

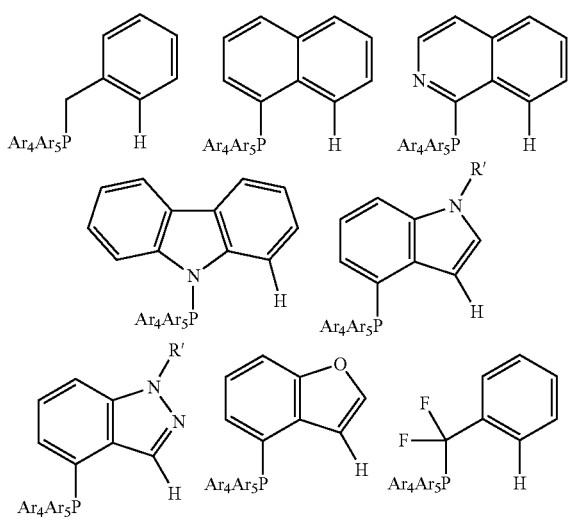

These carbon-phosphorus ligands (P^C)H, comprise of a tertiary phosphine fragment as well as an additional aromatic, heterocyclic or even alkenyl C—H moiety, the latter can react with the transition-metal reagent to lost its hydrogen atom via direct C—H bond activation and cyclometalation, giving formation of the anionic carbon-phosphorus (P^C) chelate which is stabilized by formation of both metal-phosphine dative interaction and covalent metal-carbon bonding interaction. Moreover, after reacting with the employed metal reagent, the local arrangement of carbon-phosphorus (P^C) chelate formed a five-membered, planar metallacycle, which could provide the highest stabilization to the resulting metal chelates. The relationship of five-membered metallacycle versus other less desirable, four-membered or six-membered (P^C) metallacycles is indicated below:

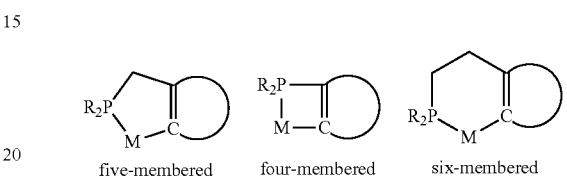

five-membered    four-membered    six-membered

It is notable that if the polyaromatic or heterocyclic fragment such as naphthalene, isoquinoline, indole and carbazole was employed to assemble the carbon-phosphorus (C^P) chelate, due to the relatively smaller ππ* energy gap associated with these fragments, the chelate dominating the lowest energy excited states would be shifted from the previously mentioned (C^N) or (N^N) chelates to the ancillary (P^C) chelate. Alternatively, if we selected the (C^N) and (N^N) chelates with a much greater degree of m-conjugation, c.f. that of 1-phenyl isoqunioline, 1-phenyl quinazoline and 3-tert-butyl-5-(1-isoquniolinyl)pyrazole, these chromophoric chelates would regain the dominance of emissive properties of the assembled Ir(III) metal complexes, giving a significantly better emission efficiency in both fluid and solid states.

Moreover, a preferred synthesis of the emissive iridium (III) complexes with the formula [(C^N)$_2$Ir(P^C)] comprises the following procedures:

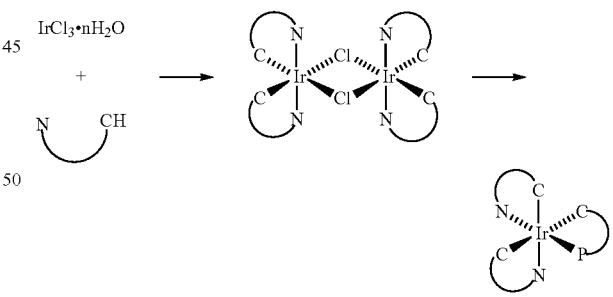

The first step involved the thermal treatment of two equiv. of (N^C)H with IrCl$_3$·nH$_2$O in methoxyethanol to afford the dimer [(C^N)$_2$Ir(μ-Cl)]$_2$ as intermediate. After then, reaction of this dimer with the carbon-phosphorus chelate (C^P)H in high boiling decalin and in presence of excess sodium acetate as HCl scavenger would initiate coordination of (C^P) chelate, followed by cyclometalation to afford the desired heteroleptic complex of formula [(C^N)$_2$Ir(C^P)].

Alternatively, the emissive iridium (III) complexes with the formula [(N^N)Ir(P^C)$_2$] is best conducted employing the distinctive sequences:

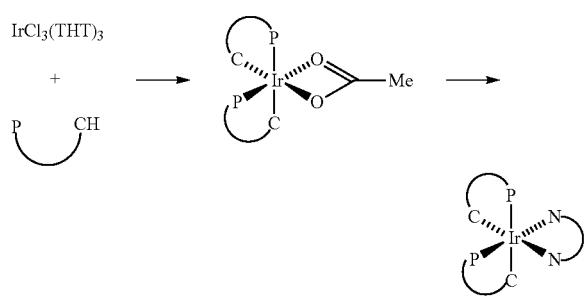

In this reaction sequence, a distinctive iridium reagent $IrCl_3(THT)_3$ was selected due to its increased solubility in high boiling hydrocarbon solvent such as decalin. Thus, treatment of $IrCl_3(THT)_3$ with two equiv. of (C^P)H in presence of sodium acetate would give isolation of the intermediate [(C^P)$_2$Ir(OAc)] in high yields. This intermediate can be fully characterized by spectroscopic means and in one case, by single crystal X-ray diffraction study. Subsequent treatment of [(C^P)$_2$Ir(OAc)] with (N^N)H chelate produced the expected ligand exchange and formation of [(N^N)Ir(P^C)$_2$] in moderate yields. Alternatively, the reaction sequence can be simplified by skipping isolation of [(C^P)$_2$Ir(OAc)]; thus, a one-pot procedure can be attained by further lowering the cost for its production.

Moreover, if the polyaromatic or heterocyclic fragment such as naphthalene, isoquinoline, indole and carbazole was employed to assemble the carbon-phosphorus (C^P) chelate, the resulting (C^P)H ligands are only suitable for preparation of emissive metal complexes showing longer wavelength phosphorescence, typically in the region from orange to red. This is due to the smaller $\pi\pi^*$ energy gap associated with the polyaromatic and heterocyclic fragments that, in turn, would dominate the lowest energy excited states of the tris-chelated metal complexes. If such situation occurred, (C^N) or (N^N) chelates should no longer be considered as the chromophoric ligands of the metal complexes.

Despite of this uncertainty in describing the exact characteristics of excited states, the resulting emissive metal complexes retain it charge-neutral characteristics and greater volatility under reduced pressure or in vacuo at elevated temperature. These physical properties are essentially for the subsequent fabrication of OLEDs employing direct thermal evaporation.

The present invention provides the phosphorescent metal complexes with carbon-phosphorus ancillary chelate(s) and chromophoric ligand(s), synthetic method of preparing the same and phosphorescent organic light emitting diode thereof for enhancing the quantum efficiency, synthetic yield of the iridium complexes and the luminous efficiency of phosphorescent OLEDs.

DETAILED DESCRIPTION OF THE INVENTION

Figure 1:
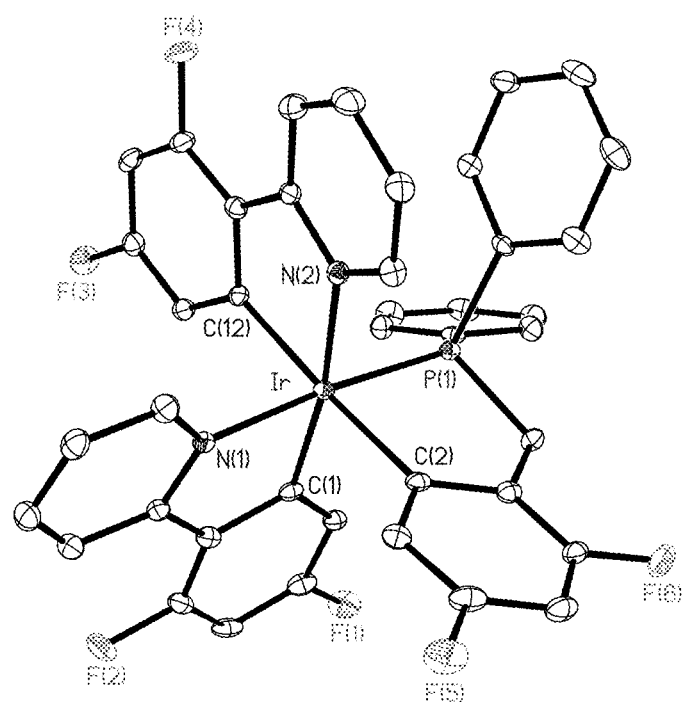
FIG. 1 shows the x-ray structure of an Ir complex (2) synthesized in Example 1 according to the present invention.

The present invention provides a phosphorescent tris-chelated transition metal complex comprising i) two identical carbon-nitrogen (C^N) or nitrogen-nitrogen (N^N) chelates being incorporated into a coordination sphere thereof with a transition metal, and one carbon-phosphorus (C^P) chelate being incorporated into the coordination sphere; or ii) one carbon-nitrogen (C^N) or nitrogen-nitrogen (N^N) chelate forming a coordination sphere thereof with a transition metal, and two identical carbon-phosphorus (C^P) chelates being incorporated into the coordination sphere, wherein the transition metal is iridium, platinum, osmium or ruthenium, and iridium is preferable.

Preferably, the complex of the present invention is represented by the following formulas Ia, Ib, Ic, Id or their stereo isomers:

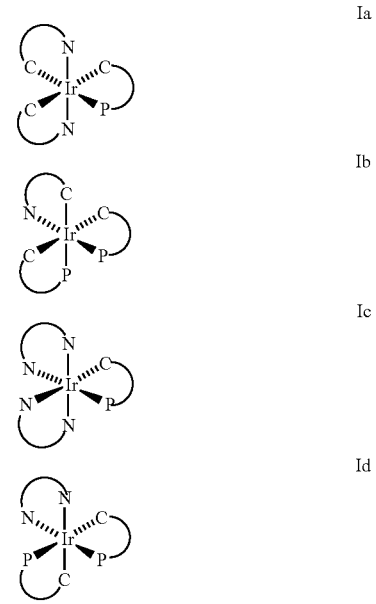

wherein the C and N linked with an arch, or N and N linked with an arch have a formula of $Ar^1$—$Ar^2$, wherein $Ar^1$ is aromatic ring or a N-heterocyclic ring, and $Ar^2$ is N-heterocyclic ring, wherein C in the formulas Ia and Ib is a carbon atom contained in the aromatic ring of $Ar^1$ and N in the formulas Ia and Ib is a nitrogen atom contained in $Ar^2$, N in the formulas Ic and Id is a nitrogen atom contained in the heterocyclic rings of $Ar_1$ and $Ar^2$; the carbon-phosphorus (C^P) chelates are presented by the P and C linked with an arch, and have a formula of $Ar^3$—$(C(R^4R^5))_m$—$P(Ar^4Ar^5)$, wherein m is 0, 1 or 2; $Ar^4$ and $Ar^5$ independently are phenyl, functionalized phenyl, iso-propyl or tert-butyl; $R^4$ and $R^5$ independently are H or methyl; —$Ar^3$ is

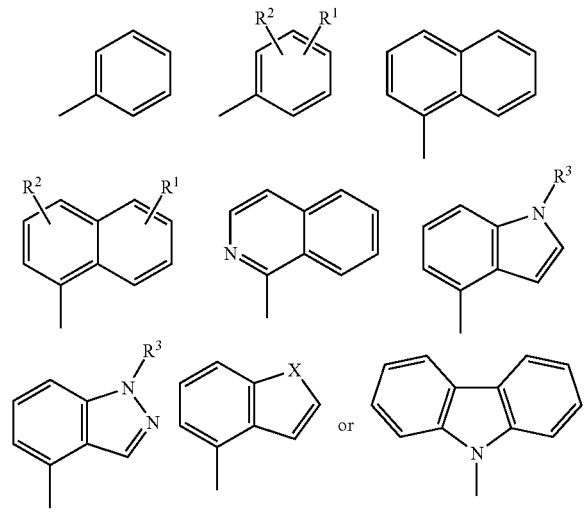

wherein $R^1$ and $R^2$ independently are alkyl, cyano, F or $C_nF_{2n+1}$, n is an integer of 1-3; $R^3$ is methyl, phenyl, alkyl, cyano, and functionalized aromatic group; and X is oxygen or sulfur.

Preferably, the carbon-phosphorus (C^P) chelates are

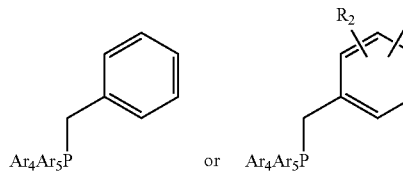

More preferably, $Ar^4$ and $Ar^5$ are both phenyl, and $R^1$ and $R^2$ are both F.

Preferably, the carbon-phosphorus (C^P) chelates are

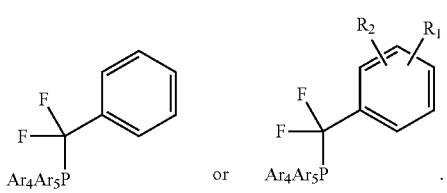

More preferably, $Ar^4$ and $Ar^5$ are both phenyl, and $R^1$ and $R^2$ are both F.

Preferably, the carbon-phosphorus (C^P) chelates are

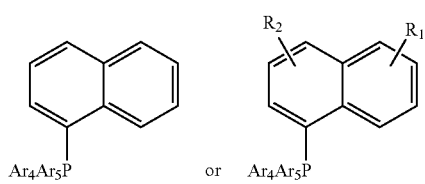

More preferably, $Ar^4$ and $Ar^5$ are both phenyl, and $R^1$ and $R^2$ are both F.

Preferably, the carbon-phosphorus (C^P) chelates are

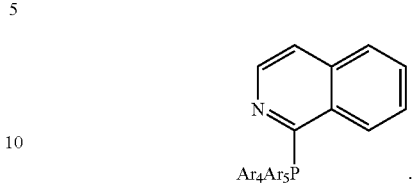

More preferably, $Ar^4$ and $Ar^5$ are both phenyl. Alternatively, the nitrogen atom is relocated to other position except at the 8-position.

Preferably, the carbon-phosphorus (C^P) chelates are

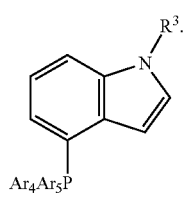

More preferably, $Ar^4$, $Ar^5$ and $R^3$ are all phenyl.

Preferably, the carbon-phosphorus (C^P) chelates are

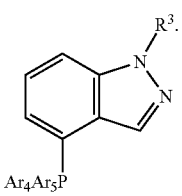

More preferably, $Ar^4$, $Ar^5$ and $R^3$ are all phenyl.

Preferably, the carbon-phosphorus (C^P) chelates are

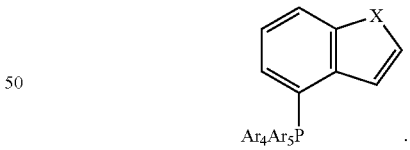

More preferably, $Ar^4$ and $Ar^5$ are phenyl.

Preferably, the carbon-phosphorus (C^P) chelates are

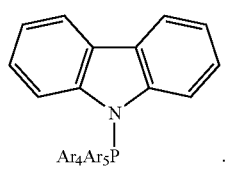

More preferably, $Ar^4$ and $Ar^5$ are phenyl.

Preferably, the carbon-nitrogen (C^N) chelates are

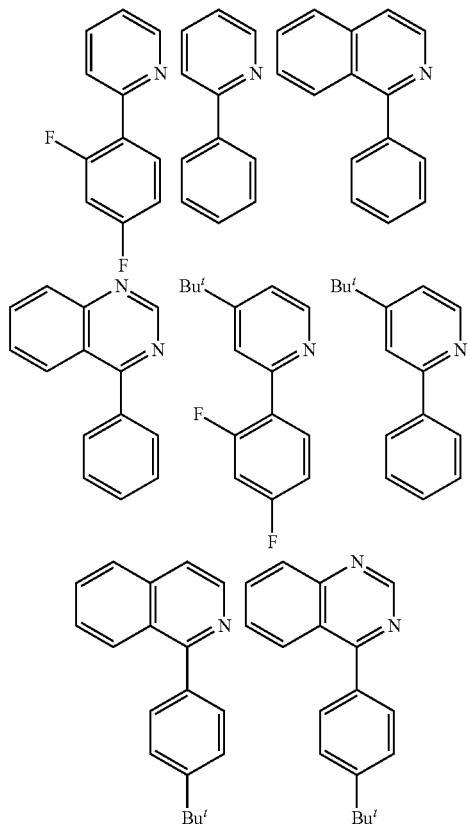

wherein Bu$^t$ is tert-butyl.

Preferably, the nitrogen-nitrogen (N^N) chelates are

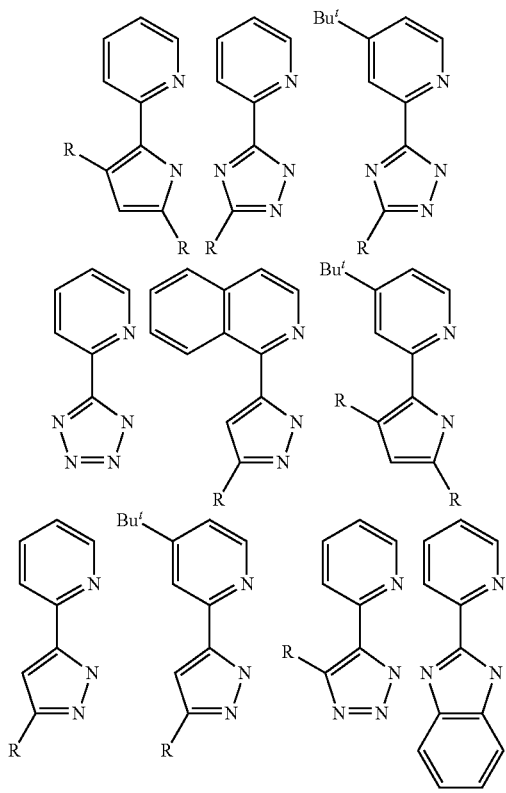

wherein R is CF$_3$, tert-butyl, phenyl or functionalized phenyl group, and Bu$^t$ is tert-butyl.

The present invention also provides a phosphorescent organic light emitting diode employing the phosphorescent tri-substituted metal chelate of the present invention as an emitting or emitter dopant material.

As for the design of phosphorescent metal complexes, they comprises the tri-substituted chelating arrangement with one or even two carbon-phosphorus (C^P) cyclometalated chelates into the coordination sphere, together with at least one (C^N) or (N^N) chelate(s), for the adjustment of emission color. It is expected that the electronic transitions that produced the emission will be principally confined to the chromophoric ligands that possess a slightly lowered energy gap (such as the energy gap for blue, green or red emission), due to the effective blocking of the ligand-to-ligand energy transfer process, as well as suppressing the unwanted thermal population to the higher lying, nonradiative metal-centered dd excited state. Thus, this molecular design would suppress the unwanted LLCT processes and give an enhanced emission quantum yield compared with all other emissive metal complexes without the carbon-phosphorus (C^P) cyclometalated chelate(s).

The present invention will be better understood through the following examples, where are for illustrative only and not for limiting the scope of the present invention.

EXAMPLE 1

Synthesis of Ir(III) Complexes with Benzyldiphenylphosphine as Carbon-Phosphorus Chelate General Experimental Procedures.

All reactions were performed under a nitrogen atmosphere using anhydrous solvents or solvents treated with an appropriate drying reagent. Mass spectra were obtained on a JEOL SX-102A instrument operating in electron impact (EI) mode or fast atom bombardment (FAB) mode. $^1$H and $^{19}$F NMR spectra were recorded on Varian Mercury-400 or INOVA-500 instruments. Elemental analyses were conducted at the NSC Regional Instrumentation Center at National Chiao Tung University, Taiwan.

X-Ray Diffraction Studies.

Single crystal X-ray diffraction data were measured on a Bruker SMART Apex CCD diffractometer using (Mo—K$_\alpha$) radiation ($\lambda$=0.71073 Å). The data collection was executed using the SMART program. Cell refinement and data reduction were performed with the SAINT program. The structure was determined using the SHELXTL/PC program and refined using full-matrix least squares.

Spectral and Dynamic Measurement.

Steady-state absorption and emission spectra were recorded by a Hitachi (U-3310) spectrophotometer and an Edinburgh (FS920) fluorimeter, respectively. Emission quantum yields were measured at excitation wavelength $\lambda_{ex}$=350 nm in CH$_2$Cl$_2$ at room temperature. In this approach, Quinine sulfate with an emission yield of $\Phi$~0.54±0.2 in 1.0N sulfuric acid solution served as the standard to calculate the emission quantum yield. Lifetime studies were performed by an Edinburgh FL 900 photon counting system with a hydrogen-filled or a nitrogen lamp as the excitation source. Data were analyzed using a nonlinear least squares procedure in combination with an iterative convolution method. The emission decays were analyzed by the sum of exponential functions, which allows partial removal of the instrument time broadening and consequently renders a temporal resolution of ~200 ps.

Synthesis of [Ir(dfppy)₂(bdp)] (1)

Benzyldiphenylphosphine (bdpH, 61 mg, 0.22 mmol), [(dfppy)₂Ir(μ-Cl)]₂ (122 mg, 0.10 mmol) and sodium acetate (82 mg, 1.00 mmol) were combined in degassed decalin (30 mL) and the mixture was refluxed for 26 hour. After cooling to RT and removal of solvent, the residue was purified by silica gel column chromatography using a 1:3 mixture of ethyl acetate and hexane as the eluent. The pale yellow crystals were obtained by slow diffusion of hexane into a CH₂Cl₂ solution at RT (70 mg, 0.08 mmol, 41%).

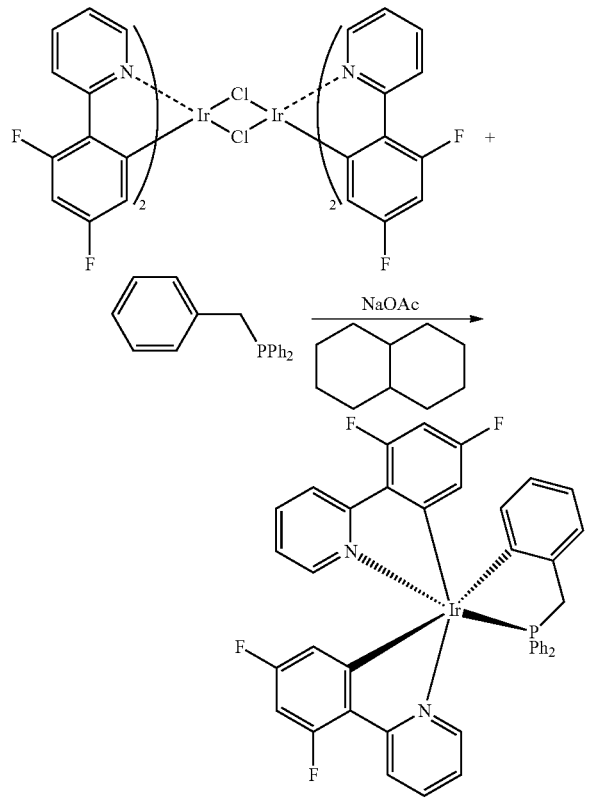

Spectral Data of (1):

MS (FAB, $^{193}$Ir): m/z 848 (M+1)$^+$; $^1$H NMR (500 MHz, CDCl₃, 294K): δ 8.17 (d, J=9.5 Hz, 1H), 8.05 (d, J=8.5 Hz, 1H), 7.55~7.64 (m, 4H), 7.36~7.40 (m, 3H), 7.28 (t, J=7.5 Hz, 2H), 6.93 (t, J=7.5 Hz, 1H), 7.37 (t, J=7.0 Hz, 1H), 6.72~6.83 (m, 6H), 6.62~6.66 (m, 3H), 6.38~6.43 (m, 1H), 6.27~6.35 (m, 3H), 4.32 (dd, J=15.5, 8.0 Hz, 1H), 4.21 (t, J=15.0, 1H). $^{19}$F-{$^1$H} NMR (376 MHz, CDCl₃, 294K): δ −110.03 (m, 2F), −110.23 (d, J=10.9 Hz, 1F), −110.28 (d, J=9.0 Hz, 1F). $^{31}$P-{$^1$H} NMR (202 MHz, CDCl₃, 294K): δ 13.34 (s, 1P).

Synthesis of [Ir(dfppy)₂(dfbdp)] (2)

(2,4-difluorobenzyl)diphenylphosphine (dfbdpH, 69 mg, 0.22 mmol), [(dfppy)₂Ir(μ-Cl)]₂ (122 mg, 0.10 mmol) and sodium acetate (82 mg, 1.00 mmol) were combined in degassed decalin (30 mL) and the mixture was refluxed for 26 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH₂Cl₂ solution at RT (82 mg, 0.09 mmol, 46%).

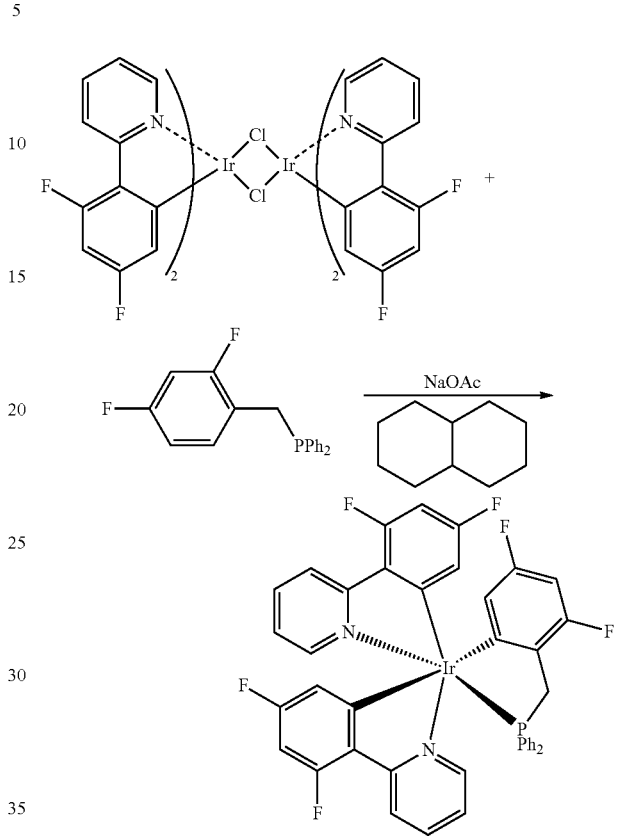

Spectral Data of (2):

MS (FAB, $^{193}$Ir): m/z 885 (M$^+$); $^1$H NMR (500 MHz, CDCl₃, 294K): δ 8.21 (d, J=9.0 Hz, 1H), 8.06 (d, J=8.0 Hz, 1H), 7.60~7.65 (m, 3H), 7.51 (d, J=5.5 Hz, 1H), 7.42 (t, J=8.0 Hz, 1H), 7.38 (d, J=7.5 Hz, 1H), 7.29 (t, J=7.0 Hz, 2H), 7.19~7.21 (m, 1H), 6.91 (t, J=7.0 Hz, 1H), 6.85 (t, 6.5 Hz, 1H), 6.78 (t, J=6.0 Hz, 3H), 6.56~6.62 (m, 3H), 6.33~6.44 (m, 4H), 5.75 (d, J=9.0 Hz, 1H), 4.43 (t, J=15.5 Hz, 1H), 3.94 (dd, J=17.0, 7.5 Hz, 1H). $^{19}$F-{$^1$H} NMR (376 MHz, CDCl₃, 294K): δ −109.25 (d, J=10.5 Hz, 1F), −109.75 (m, 4F), −115.50 (d, J=6.0 Hz, 1F). $^{31}$P-{$^1$H} NMR (202 MHz, CDCl₃, 294K): δ 14.71 (s, 1P).

Synthesis of [Ir(piq)₂(bdp)] (3)

Benzyldiphenylphosphine (bdpH, 61 mg, 0.22 mmol), [(piq)₂Ir(μ-Cl)]₂ (127 mg, 0.10 mmol) and sodium acetate (82 mg, 1.00 mmol) were combined in degassed decalin (30 mL) and the mixture was refluxed for 36 hour. After cooling to RT and removal of solvent, the residue was purified by silica gel column chromatography using a 1:3 mixture of ethyl acetate and hexane as the eluent. The pale yellow crystals were obtained by slow diffusion of hexane into a CH₂Cl₂ solution at RT (87 mg, 0.07 mmol, 28%). [The abbreviation of piqH represents phenyl isoquinoline.]

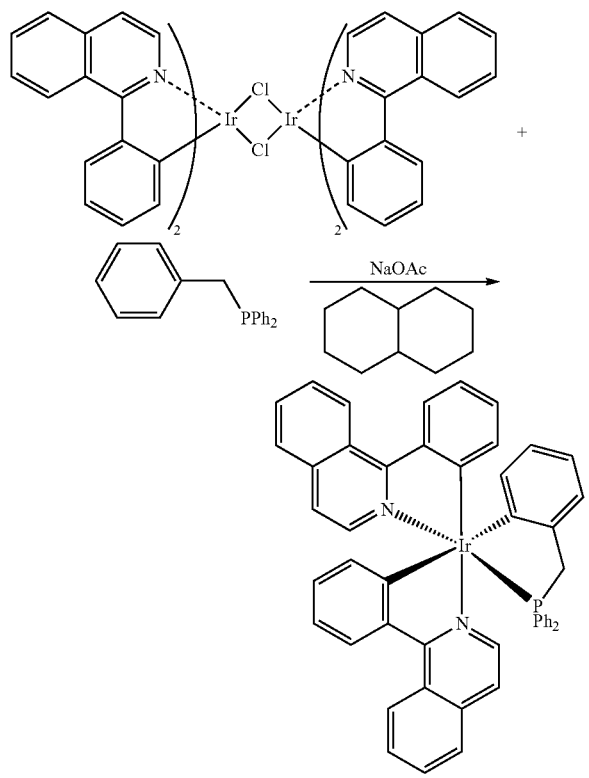

Spectral Data of (3):
MS (FAB, $^{193}$Ir): m/z 892 (M+1)$^+$; $^1$H NMR (500 MHz, CDCl$_3$, 294K): δ 8.79 (d, J=9.5 Hz, 1H), 8.76 (d, J=8.5 Hz, 1H), 8.12 (d, J=8.0 Hz, 1H), 8.08 (d, J=7.5 Hz, 1H), 7.79~7.83 (m, 2H), 7.43 (d, J=6.0 Hz, 1H), 7.66 (d, J=8.5 Hz, 1H), 7.54~7.59 (m, 6H), 7.42 (dd, J=6.5, 2.5 Hz, 1H), 7.32~7.36 (m, 2H), 7.25~7.27 (m, 2H), 7.13 (dd, J=7.0, 1.0 Hz, 1H), 7.00 (d, J=6.5 Hz, 1H), 6.92~6.96 (m, 2H), 6.89 (dd, J=7.0, 1.0 Hz, 1H), 6.84 (t, J=7.5 Hz, 1H), 6.75 (td, J=7.5, 1.5 Hz, 1H), 6.62~6.66 (m, 2H), 6.51 (t, J=9.0 Hz, 2H), 6.38 (td, J=7.5, 1.5 Hz, 1H), 6.22~6.26 (m, 3H), 4.35 (dd, J=16.0, 9.0 Hz, 1H), 4.21 (dd, J=16.0, 13.0 Hz, 1H). $^{31}$P-{$^1$H} NMR (202 MHz, CDCl$_3$, 294K): δ 15.12 (s, 1P).

Synthesis of [Ir(dfpbpy)$_2$(dfbdp)] (4)

this sample was synthesized using procedures similar to those used in the synthesis of (2).

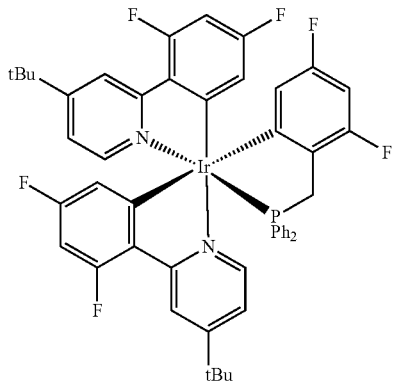

Spectral Data of (4):
MS (FAB, $^{193}$Ir): m/z 885 (M+1)$^+$; $^1$H NMR (500 MHz, CDCl$_3$, 294K): δ 8.21 (s, 1H), 8.08 (s, 1H), 7.63 (t, J=8.5 Hz, 2H), 7.36~7.39 (m, 2H), 7.29 (t, J=6.5 Hz, 2H), 7.13 (dd, J=6.0, 3.5 Hz, 1H), 6.90 (d, J=7.0 Hz, 1H), 6.87 (d, J=7.0 Hz, 1H), 6.75~6.78 (m, 3H), 6.63 (dd, J=7.5, 2.0 Hz, 1H), 6.57 (t, J=9.0 Hz, 2H), 6.33~6.44 (m, 4H), 5.75 (dd, J=5.5, 1.5 Hz, 1H), 4.41 (t, J=15.0 Hz, 1H), 3.92 (dd, J=16.0, 7.0 Hz, 1H), 1.28 (s, 9H), 1.23 (s, 9H). $^{19}$F-{$^1$H} NMR (376 MHz, CDCl$_3$, 294K): δ −110.08 (m, 2F), −110.18 (d, J=9.4 Hz, 1F), −110.22 (d, J=10.2 Hz, 1F), −110.52 (d, J=9.4 Hz, 1F), −115.80 (d, =5.6 Hz, 1F). $^{31}$P-{$^1$H} NMR (202 MHz, CDCl$_3$, 294K): δ 14.83 (s, 1P).

Figure 2:
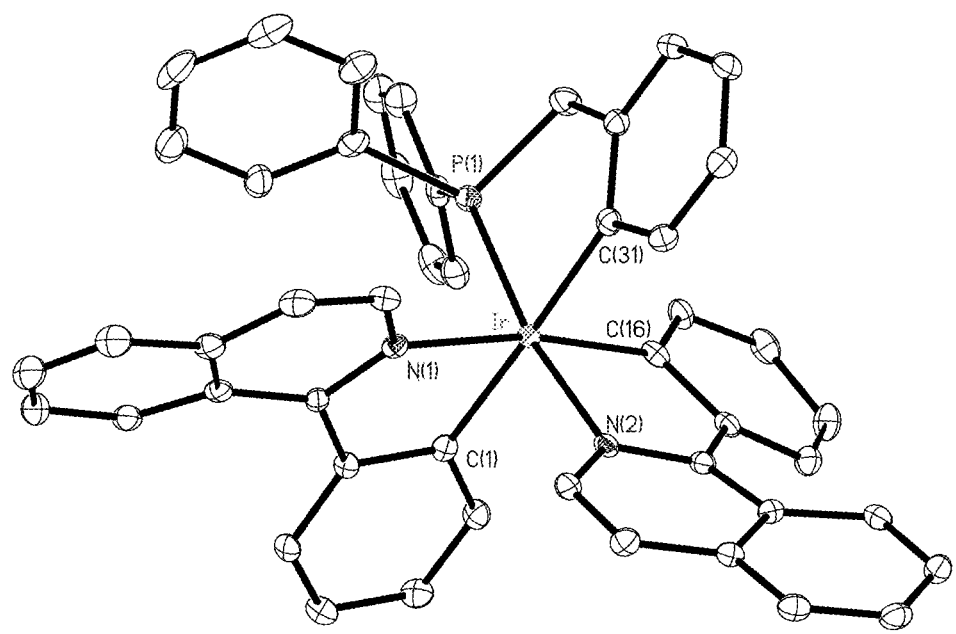
FIG. 2 shows the x-ray structure of an Ir complex (3) synthesized in Example 1 according to the present invention.

The molecular structures of (2) and (3) are shown in FIGS. 1 and 2, respectively. Selected photophysical properties of complexes prepared in Example 1 were measured in degassed CH$_2$Cl$_2$ solution at room temperature, and are shown in Table 1.

TABLE 1

| | PL (in degassed CH$_2$Cl$_2$) | | | | |
|---|---|---|---|---|---|
| Sample | λ$_{max}$ (nm) | Q.Y. | τ$_{obs}$ (ns) | k$_r$ | k$_{nr}$ |
| (1) | 469 | 6.1 | 145 | 4.2 × 10$^5$ | 6.5 × 10$^6$ |
| (2) | 457, 481 | 19 | 490 | 3.9 × 10$^5$ | 1.7 × 10$^6$ |
| (3) | 600 | 86 | 3440 | 2.5 × 10$^5$ | 4.1 × 10$^4$ |
| (4) | 456, 480 | 67 | 1420 | 4.7 × 10$^5$ | 2.3 × 10$^5$ |

Figure 3:
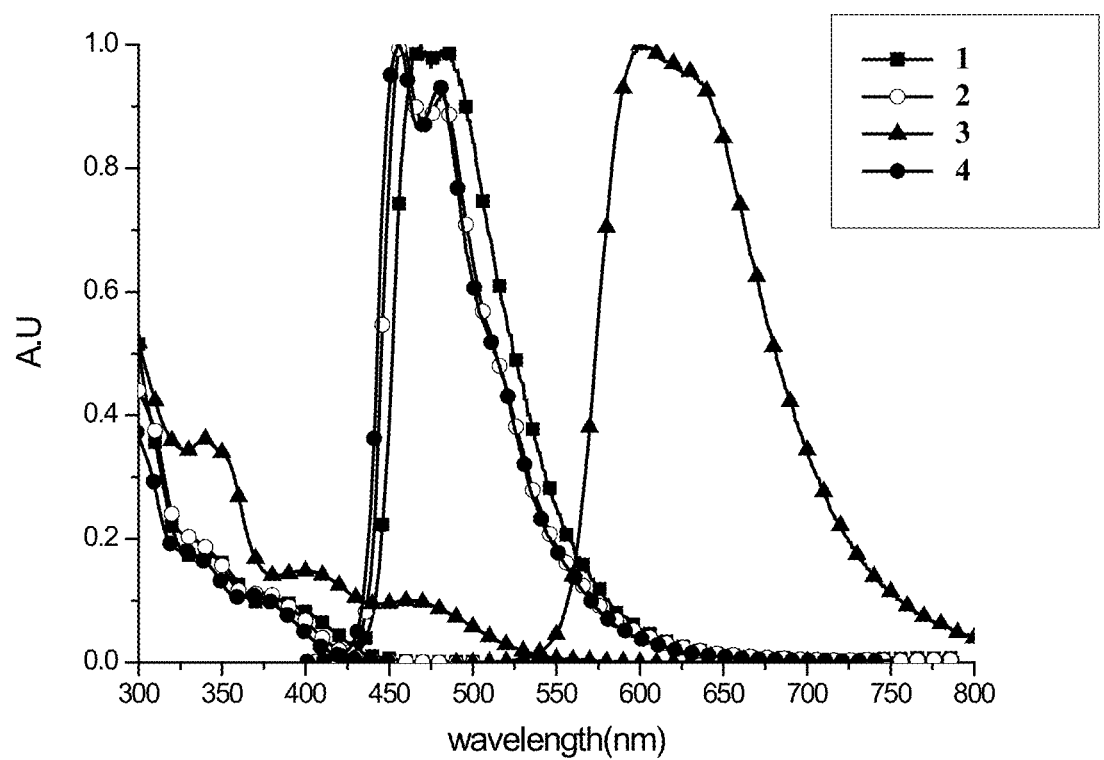
FIG. 3 shows the UV/vis absorption and emission spectra of the complexes (1)-(4) in $CH_2Cl_2$ solution, which were prepared in Example 1 according to the present invention.

FIG. 3 shows the UV/vis absorption and emission spectra of the complexes prepared in Example 1 in CH$_2$Cl$_2$ solution.

EXAMPLE 2

Synthesis of Ir(III) Complexes with Dual Carbon-Phosphorus Chelates

Synthesis of [Ir(dfbdp)$_2$(OAc)] (5)

IrCl$_3$(THT)$_3$ (110 mg, 0.20 mmol), (2,4-difluorobenzyl)diphenylphosphine (dfbdpH, 137 mg, 0.44 mmol), and sodium acetate (164 mg, 2.00 mmol) were combined in degassed decalin (15 mL) and the mixture was refluxed for 3 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (135 mg, 0.15 mmol, 76%).

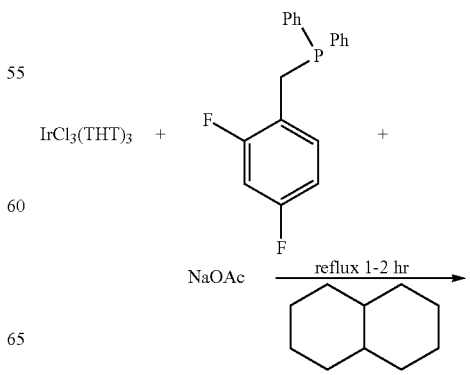

-continued

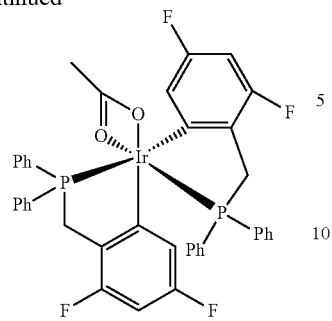

Spectral Data of (5):

MS (FAB, $^{193}$Ir): m/z 890 (M+1)$^+$; $^1$H NMR (500 MHz, CDCl$_3$, 294K): δ 7.58~7.62 (m, 4H), 7.40~7.44 (m, 2H), 7.29~7.35 (m, 3H), 7.23~7.27 (m, 3H), 7.18~7.22 (m, 2H), 7.06~7.10 (m, 1H), 6.89~6.93 (m, 2H), 6.84 (td, J=8.0, 2.5 Hz, 1H), 6.53 (t, J=9.5 Hz, 1H), 6.42 (td, J=10.0, 2.0 Hz, 1H), 6.26 (dd, J=10.5, 1.0 Hz, 1H), 6.10~6.13 (m, 2H), 6.26 (dd, J=10.5, 1.0 Hz, 1H), 3.59 (dd, J=16.0, 9.5 Hz, 1H), 3.29~3.37 (m, 2H), 1.09 (ddd, J=16.0, 8.0, 2.0 Hz, 1H). $^{19}$F-{$^1$H} NMR (376 MHz, CDCl$_3$, 294K): δ −108.99 (d, J=6.8 Hz, 1F), −109.18 (dd, J=9.8, 5.6 Hz, 1F), −113.94 (t, J=6.0 Hz, 1F), −114.95 (d, J=6.0 Hz, 1F). $^{31}$P-{$^1$H} NMR (202 MHz, CDCl$_3$, 294K) δ 29.10~29.21 (m, 1P), 11.63 (d, J=6.5 Hz, 1P).

Figure 4:
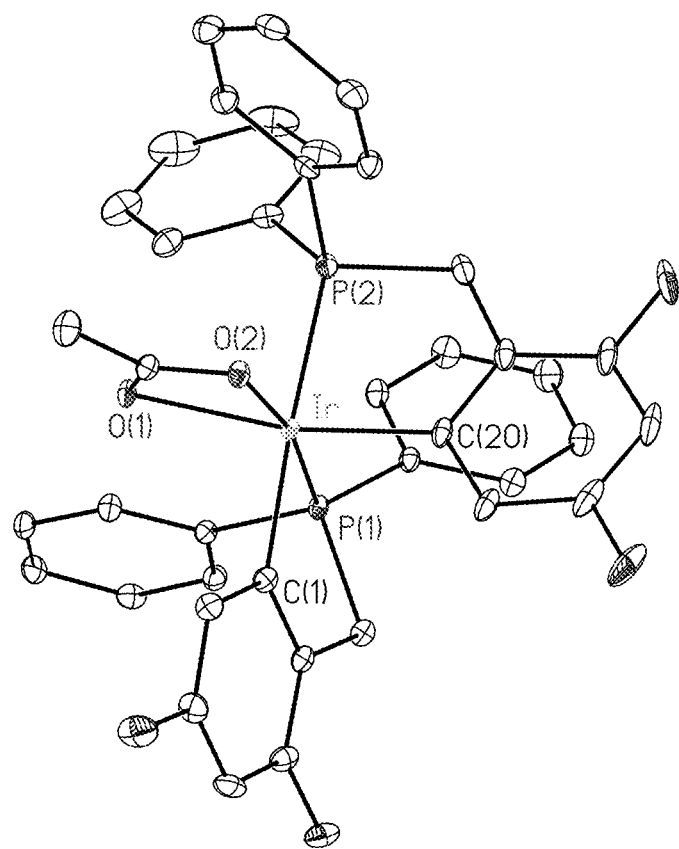
FIG. 4 shows the x-ray structure of an Ir complex (5) synthesized in Example 2 according to the present invention.

The molecular structure of [Ir(dfbdp)$_2$(OAc)] (5) is shown in FIG. 4.

Synthesis of [Ir(dfbdp)$_2$(fbptz)] (6)

IrCl$_3$(THT)$_3$ (110 mg, 0.20 mmol), (2,4-difluorobenzyl) diphenylphosphine (dfhdpH, 137 mg, 0.44 mmol), and sodium acetate (164 mg, 2.00 mmol) were combined in degassed decalin (15 mL) and the mixture was refluxed for 2 hour. After cooling to RT, 3-(trifluoromethyl)-5-(4-t-butylpyridyl)trazolate (fbptzH) (60 mg, 0.22 mmol) was added and mixture was refluxed for 6 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (125 mg, 0.12 mmol, 58%).

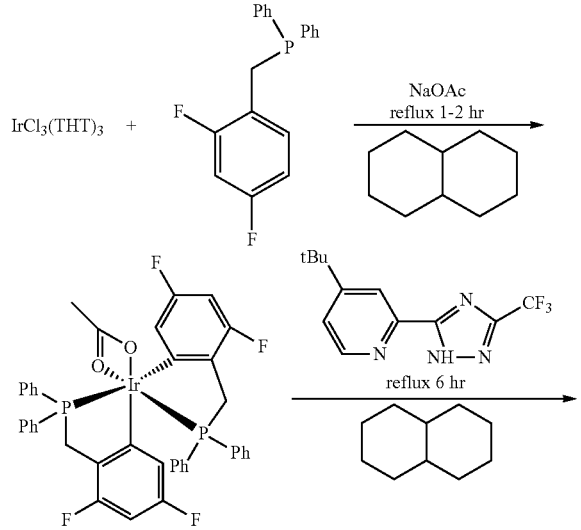

-continued

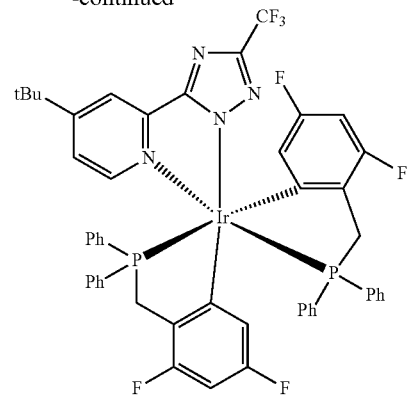

Spectral Data of (6):

MS (FAB, $^{193}$Ir): m/z 1085 (M+1)$^+$; $^1$H NMR (500 MHz, CDCl$_3$, 294K): δ 8.02 (d, J=2.0 Hz, 1H), 7.60 (d, J=6.0 Hz, 1H), 7.42~7.46 (m, 2H), 7.25~7.34 (m, 5H), 7.20 (td, J=8.0, 2.0 Hz, 2H), 7.09 (t, J=8.0 Hz, 1H), 7.02~7.06 (m, 4H), 6.90 (td, J=7.5, 2.0 Hz, 2H), 6.84 (dd, J=6.0, 2.5 Hz, 1H), 6.72 (t, J=8.5 Hz, 2H), 6.43~6.50 (m, 3H), 6.31~6.36 (m, 2H), 5.57~5.61 (m, 1H), 4.01 (dd, J=17.0, 11.0 Hz, 1H), 3.84 (t, J=12.5 Hz, 1H), 3.77 (dd, J=16.5, 9.5 Hz, 1H), 2.66 (dd, J=16.5, 8.5 Hz, 1H), 1.33 (s, 9H). $^{19}$F-{$^1$H} NMR (376 MHz, CDCl$_3$, 294K): δ −63.37 (s, 3F), −109.39 (dd, J=9.8, 5.3 Hz, 1F), −110.61 (d, J=5.3 Hz, 1F), −112.52 (t, J=6.4 Hz, 1F), −115.19 (d, J=5.6 Hz, 1F). $^{31}$P-{$^1$H} NMR (202 MHz, CDCl$_3$, 294K): δ 8.72 (d, J=10.1 Hz, 1P), 6.30~6.44 (m, 1P).

Synthesis of [Ir(dfbdp)$_2$(fptz)] (7)

IrCl$_3$(THT)$_3$ (110 mg, 0.20 mmol), (2,4-difluorobenzyl) diphenylphosphine (dfbdpH, 137 mg, 0.44 mmol), and sodium acetate (164 mg, 2 mmol) were combined in degassed decalin (15 mL) and the mixture was refluxed for 2 hour. After cooling to RT, 5-pyridyl-3-trifluoromethyl-1,2,4-triazole (fptzH) (47 mg, 0.22 mmol) was added and mixture was refluxed for 6 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (102 mg, 0.10 mmol, 50%).

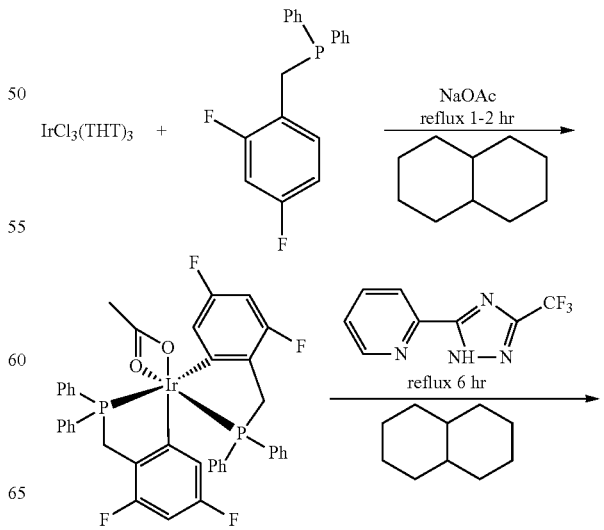

-continued

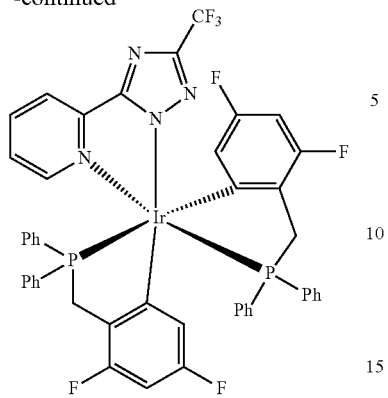

Spectral Data of (7):

MS (FAB, $^{193}$Ir): m/z 1029 (M+1)$^+$; $^1$H NMR (500 MHz, CDCl$_3$, 294K): δ 7.83 (t, J=7.5 Hz, 2H), 7.79 (d, J=7.5 Hz, 1H), 7.55 (t, J=7.5 Hz, 1H), 7.48~7.49 (m, 1H), 7.40~7.44 (m, 2H), 7.36 (t, J=8.0 Hz, 2H), 7.27 (t, J=7.5 Hz, 1H), 7.17~7.21 (m, 4H), 6.87~6.93 (m, 3H), 6.74 (t, J=6.5 Hz, 3H), 6.60 (t, J=9.0 Hz, 2H), 6.54 (t, J=8.5 Hz, 1H), 6.49 (dd, J=10.5, 2.0 Hz, 1H), 6.40 (td, J=9.0, 2.0 Hz, 1H), 6.20 (t, J=9.0 Hz, 2H), 5.47~5.50 (m, 1H), 3.86 (dd, 15.5, 10.0 Hz, 1H), 3.62~3.76 (m, 2H), 1.87 (dd, J=17.0, 8.0 Hz, 1H). $^{19}$F-{$^1$H} NMR (376 MHz, CDCl$_3$, 294K): δ −63.75 (s, 3F), −107.24 (d, J=6.4 Hz, 1F), −109.16 (dd, J=9.0, 5.6 Hz, 1F), −113.52 (d, J=6.4 Hz, 1F), −114.18 (t, J=6.4 Hz, 1F). $^{31}$P-{$^1$H} NMR (202 MHz, CDCl$_3$, 294K) δ 9.12~9.25 (m, 1P), 7.45 (d, J=10.3 Hz, 1P).

Synthesis of [Ir(dfbdp)$_2$(fppz)] (8)

IrCl$_3$(THT)$_3$ (110 mg, 0.2 mmol), (2,4-difluorobenzyl) diphenylphosphine (dfbdpH, 137 mg, 0.44 mmol), and sodium acetate (164 mg, 2 mmol) were combined in degassed decalin (15 mL) and the mixture was refluxed for 2 hour. After cooling to RT, 5-pyridyl-3-trifluoromethyl-1H-pyrazole (fppzH) (47 mg, 0.22 mmol) was added and mixture was refluxed for 6 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (92 mg, 0.09 mmol, 45%).

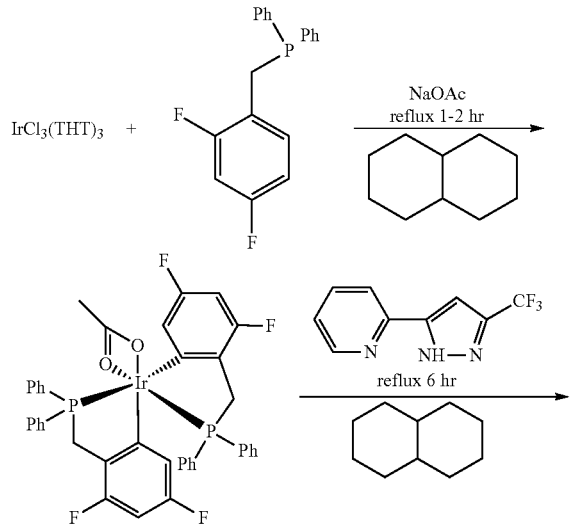

-continued

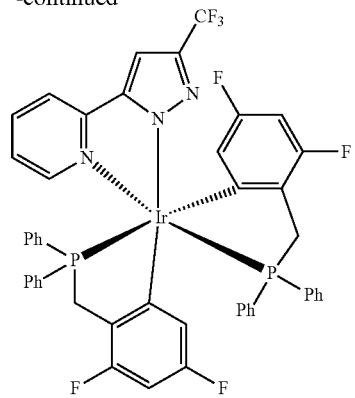

Spectral Data of (8):

MS (FAB, $^{193}$Ir): m/z 1028 (M+1)$^+$; $^1$H NMR (500 MHz, CDCl$_3$, 294K): δ 7.84 (d, J=9.0 Hz, 1H), 7.82 (d, J=9.0 Hz, 1H), 7.42 (d, J=6.0 Hz, 1H), 7.39 (d, J=7.0 Hz, 1H), 7.27~7.32 (m, 5H), 7.21 (t, J=7.5 Hz, 1H), 7.16 (t, J=6.5 Hz, 2H), 7.08 (t, J=7.0 Hz, 2H), 6.86~6.92 (m, 3H), 6.81 (s, 1H), 6.73 (t, J=7.0 Hz, 2H), 6.66 (t, J=8.5 Hz, 2H), 6.52 (t, J=6.5 Hz, 1H), 6.48 ~6.49 (m, 2H), 6.39 (td, J=9.0, 2.0 Hz, 1H), 6.31 (t, J=8.5 Hz, 2H), 5.64~5.67 (m, 1H), 3.98 (dd, J=16.0, 11.0 Hz, 1H), 3.75~3.88 (m, 2H), 2.15 (dd, J=16.5, 6.0 Hz, 1H). $^{19}$F-{$^1$H} NMR (376 MHz, CDCl$_3$, 294K): δ −60.51 (s, 3F), −108.13 (d, J=6.4 Hz, 1F), −109.92 (m, 1F), −114.19 (d, J=6.0 Hz, 1F), −114.90 (m, 1F). $^{31}$P-{$^1$H} NMR (202 MHz, CDCl$_3$, 294K): δ 6.96 (m, 2P).

Synthesis of [Ir(bdp)$_2$(fppz)] (9)

IrCl$_3$(THT)$_3$ (110 mg, 0.20 mmol), benzyl diphenylphosphine (bdpH, 122 mg, 0.44 mmol), and sodium acetate (164 mg, 2.00 mmol) were combined in degassed decalin (15 mL) and the mixture was refluxed for 2 hour. After cooling to RT, 5-pyridyl-3-trifluoromethyl-1H-pyrazole (fppzH) (47 mg, 0.22 mmol) was added and mixture was refluxed for 6 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (92 mg, 0.10 mmol, 48%).

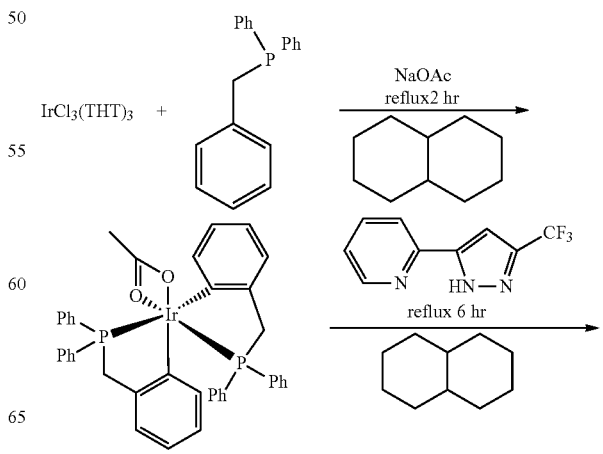

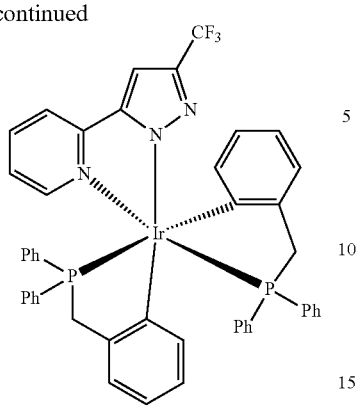
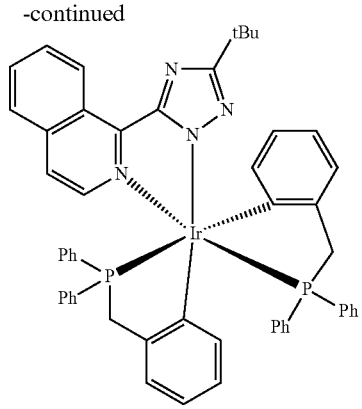

Spectral Data of (9):
MS (FAB, $^{193}$Ir): m/z 956 (M+1)$^+$; $^1$H NMR (500 MHz, CDCl$_3$, 294K): δ 7.89 (d, J=8.0 Hz, 1H), 7.87 (t, J=8.0 Hz, 1H), 7.50 (d, J=6.5 Hz, 1H), 7.43 (t, J=9.0 Hz, 2H), 7.33~7.25 (m, 3H), 7.21 (d, J=7.5 Hz, 1H), 7.15 (t, J=8.0 Hz, 3H), 7.11~7.08 (m, 5H), 6.96 (t, J=7.5 Hz, 1H), 6.85 (t, J=7.5 Hz, 1H), 6.82~6.79 (m, 3H), 6.77 (s, 1H), 6.72 (t, J=7.5 Hz, 1H), 6.69~6.66 (m, 3H), 6.61 (t, J=9.0 Hz, 2H), 6.43 (t, J=7.0 Hz, 1H), 6.32 (t, J=8.5 Hz, 21~1), 6.18 (t, J=6.0 Hz, 1H), 4.05 (dd, J=15.0, 11.0 Hz, 1H), 3.77 (dd, J=15.0, 11.0 Hz, 1H), 3.46 (dd, J=16.5, 10.0 Hz, 1H), 2.17 (dd, J=16.5, 10.0 Hz, 1H). $^{19}$F-{$^1$H} NMR (470 MHz, CDCl$_3$, 294K): δ −60.27 (s, 3F). $^{31}$P-{$^1$H} NMR (202 MHz, CDCl$_3$, 294K): δ 6.29 (d, J=11.1 Hz, 1P), 6.18 (d, J=11.1 Hz, 1P).

Figure 5:
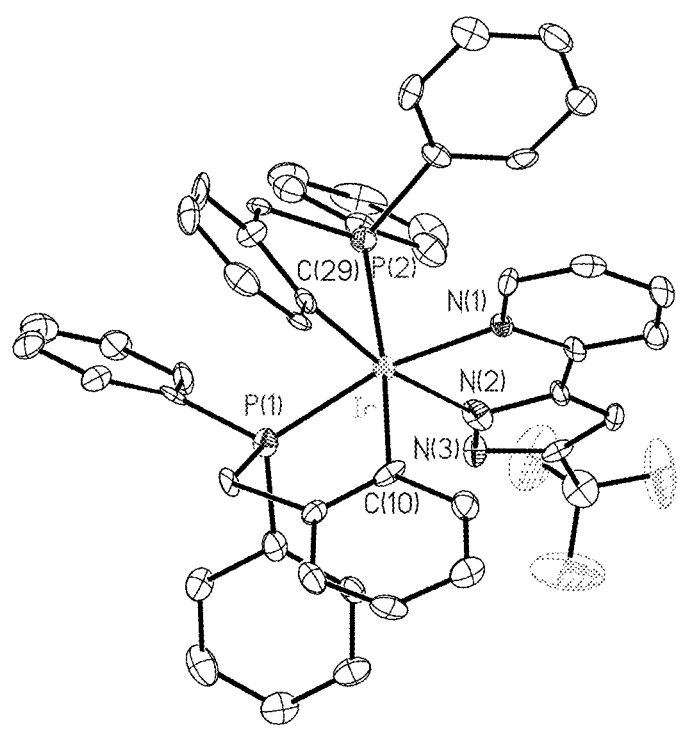
FIG. 5 shows the x-ray structure of an Ir complex (9) synthesized in Example 2 according to the present invention.

The molecular structure of [Ir(bdp)$_2$(fppz)] (9) is shown in FIG. 5.

Synthesis of [Ir(bdp)$_2$(iqbtz)] (10)

IrCl$_3$(THT)$_3$ (110 mg, 0.20 mmol), benzyldiphenyl phosphine (bdpH, 122 mg, 0.44 mmol), and sodium acetate (164 mg, 2.00 mmol) were combined in degassed decalin (15 mL) and the mixture was refluxed for 2 hour. After cooling to RT, 5-(1-isoquinolyl)-3-tert-butyl-1,2,4-triazole (iqbtzH) (56 mg, 0.22 mmol) was added and mixture was refluxed for 6 hour. After cooling to RT and removal of solvent, the residue was purified by silica gel column chromatography using a 1:1 mixture of ethyl acetate and hexane as the eluent. The pale yellow crystals were obtained by slow diffusion of hexane into a CH$_2$Cl$_2$ solution at RT (99 mg, 0.10 mmol, 50%).

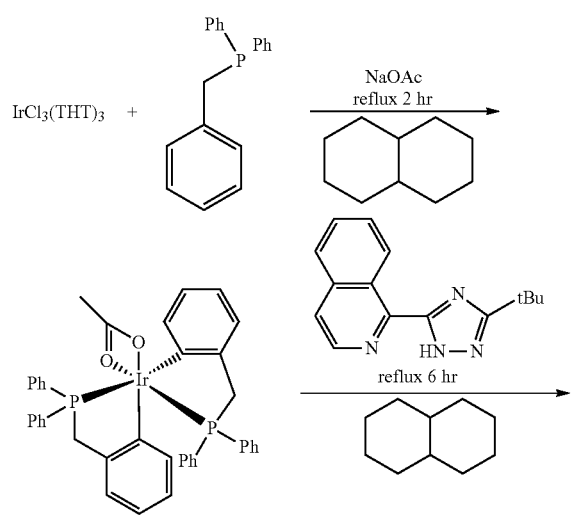

Spectral Data of (10):
MS (FAB, $^{193}$Ir): m/z 995 (M+1)$^+$; $^1$H NMR (500 MHz, CDCl$_3$, 294K): δ 10.19 (d, J=7.5 Hz, 1H), 8.23 (d, J=7.5 Hz, 1H), 8.21 (d, J=8.0 Hz, 1H), 7.70 (t, J=8.5 Hz, 2H), 7.57~7.62 (m, 2H), 7.50~7.51 (m, 2H), 7.27~7.34 (m, 2H), 7.21~7.22 (m, 3H), 7.13~7.19 (m, 3H), 7.09 (d, J=7.0 Hz, 1H), 7.06 (d, J=8.0 Hz, 1H), 7.00 (t, J=7.5 Hz, 1H), 6.75~6.83 (m, 5H), 6.58 (t, J=7.5 Hz, 1H), 6.47 (t, J=8.5 Hz, 2H), 6.34 (t, J=7.0 Hz, 2H), 6.24 (t, J=7.0 Hz, 1H), 6.14 (t, J=7.0 Hz, 1H), 6.09 (t, J=8.5 Hz, 2H), 4.22 (dd, J=14.5, 11.0 Hz, 1H), 3.53 (dd, J=15.0, 11.0 Hz, 1H), 3.36 (dd, J=17.0, 12.5 Hz, 1H), 1.89 (dd, J=16.5, 8.5 Hz, 1H), 1.52 (s, 9H). $^{31}$P-{$^1$H} NMR (202 MHz, CDCl$_3$, 294K): δ 9.25 (d, J=9.3 Hz, 1P), 8.74 (d, J=9.3 Hz, 1P).

The photophysical properties of compounds (6) to (10) are listed in Table 2.

TABLE 2

| | PL (in degassed CH$_2$Cl$_2$) | | | | |
|---|---|---|---|---|---|
| Sample | $\lambda_{max}$ (nm) | Q.Y. | $\tau_{obs}$ | $k_r$ | $k_{nr}$ |
| (6) | 453 | 0.018 | 152.36 ns | 1 × 10$^5$ | 5.5 × 10$^6$ |
| (7) | 454 | 0.0005 | 2.95 ns | 1.7 × 10$^5$ | 3.4 × 10$^8$ |
| (8) | 425, 457 | 0.0004 | 5.61 ns | 7 × 10$^4$ | 1.7 × 10$^8$ |
| (9) | 460 | 0.003 | 3.05 ns | 1.1 × 10$^6$ | 3.3 × 10$^8$ |
| (10) | 599 | 1.0 | 35.5 μs | 2.8 × 10$^4$ | — |

EXAMPLE 3

Synthesis of Ir(III) Complexes with 1-Isoquinolinyldiphenylphosphine as Carbon-Phosphorus Chelate

Synthesis of dpiq 1-chloroisoquinoline (1.95 g, 12.00 mmol), copper(I) iodide (113 mg, 0.60 mmol), cesium carbonate (7.80 g, 24.00 mmol), diphenylphosphine (2.67 g, 14.40 mmol) and toluene (40 ml, it was distilled and stored under nitrogen) were in a Schlenk tube which was under pure and dry nitrogen. The reaction mixture was heated to 100° C. for 48 h. After this had cooled to room temperature, the solution was removed in vacuum. The residue was added H$_2$O (30 mL) and extracted with ethyl acetate (40 mL×3). The organic extracts were dried over Na$_2$SO$_4$ and concentrated in vacuum. The residue was loaded on a silica gel column and eluted with 1/3 ethyl acetate/Hexane to give the product. The pale green powders were crystallized from hot CH$_2$Cl$_2$ (2.36 g, 7.54 mmol, 62%).

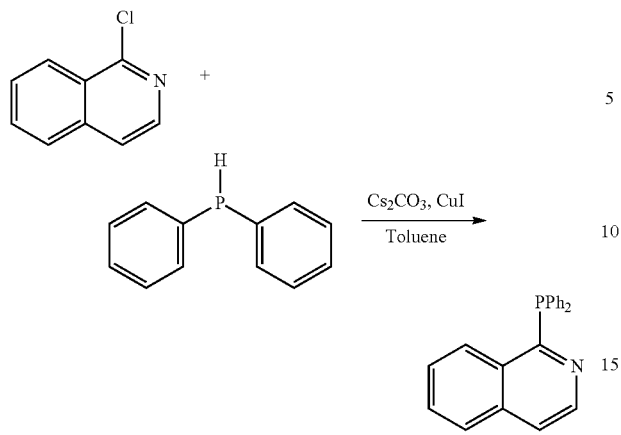

Spectral Data of dpiq: MS (ED: m/z 313 (M+); $^1$H NMR (500 MHz, CDCl$_3$, 294K): δ 8.61 (dd, J=8.0, 4.5 Hz, 1H), 8.58 (d, J=5.6 Hz, 1H), 7.80 (d, J=8.0 Hz, 1H), 7.63 (t, J=8.0 Hz, 1H), 7.56 (d, J=5.6 Hz, 1H), 7.50 (t, J=8.0 Hz, 1H), 7.36~7.44 (m, 4H), 7.28~7.34 (m, 6H). $^{31}$P-{$^1$H} NMR (202 MHz, CDCl$_3$, 294K): δ −7.18 (s, 1P).

Synthesis of [Ir(dpiq)$_2$(fppz)] (11)

IrCl$_3$(THT)$_3$ (165 mg, 0.30 mmol), 1-(diphenylphosphino)isoquinoline (dpiq, 207 mg, 0.66 mmol) and sodium acetate (246 mg, 3.00 mmol) were combined in decalin (20 mL). The reaction mixture was heated to reflux for 2 h. After this had cooled to room temperature, the mixture was added 3-trifluoromethyl-5-(2-pyridyl)pyrazole (fppzH, 64 mg, 0.30 mmol) and then heated to reflux for 9.5 h. After cooling to room temperature and removal of solvent, the residue was loaded on a silica gel column and eluted with 2/3 ethyl acetate/hexane to give the product. The pale brown crystals were obtained from CH$_2$Cl$_2$ and Methanol (100 mg. 0.10 mmol, 32%).

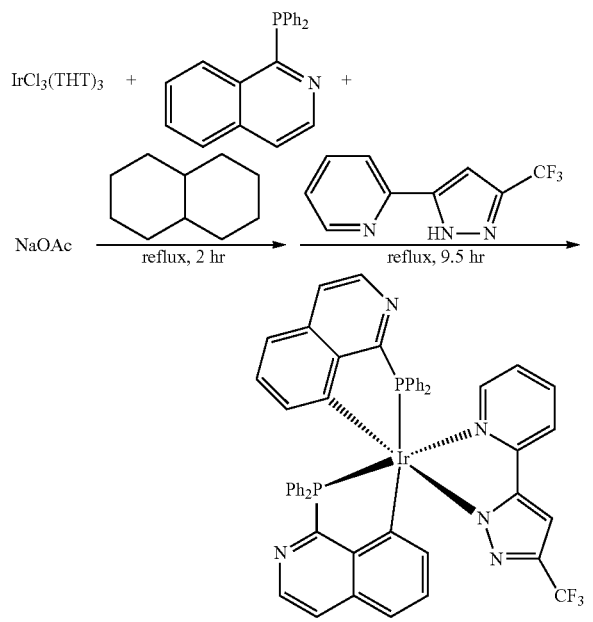

Spectral Data of (11):
MS (FAB, $^{193}$Ir): m/z 1029 (M+); $^1$H NMR (500 MHz, CDCl$_3$, 294K): δ 8.64 (t, J=8.0 Hz, 2H), 8.58 (d, J=5.5 Hz, 1H), 8.45 (d, J=5.5 Hz, 1H), 7.93 (d, J=8.0 Hz, 1H), 7.91 (d, 8.0 Hz, 1H), 7.51 (d, J=8.0 Hz, 1H), 7.44~7.49 (m, 2H), 7.32~7.40 (m, 2H), 7.20~7.31 (m, 4H), 7.14~7.20 (m, 2H), 7.12 (d, J=8.0 Hz, 1H), 7.04 (t, J=8.0 Hz, 2H), 6.78~6.88 (m, 2H), 6.72 (s, 1H), 6.56~6.62 (m, 3H), 6.50 (t, J=6.0 Hz, 1H), 6.41 (t, J=6.0 Hz, 1H), 6.28~6.34 (m, 3H), 6.12 (t, J=9.0 Hz, 2H), 5.82 (t, J=8.5 Hz, 2H). $^{19}$F-{$^1$H} NMR (470 MHz, CDCl$_3$, 294K): δ −60.80 (s, 3F). $^{31}$P-{$^1$H} NMR (202 MHz, CDCl$_3$, 294K): δ 16.17 (d, J=12.9 Hz, 1P), 12.54 (d, J=12.9 Hz, 1P).

Figure 6:
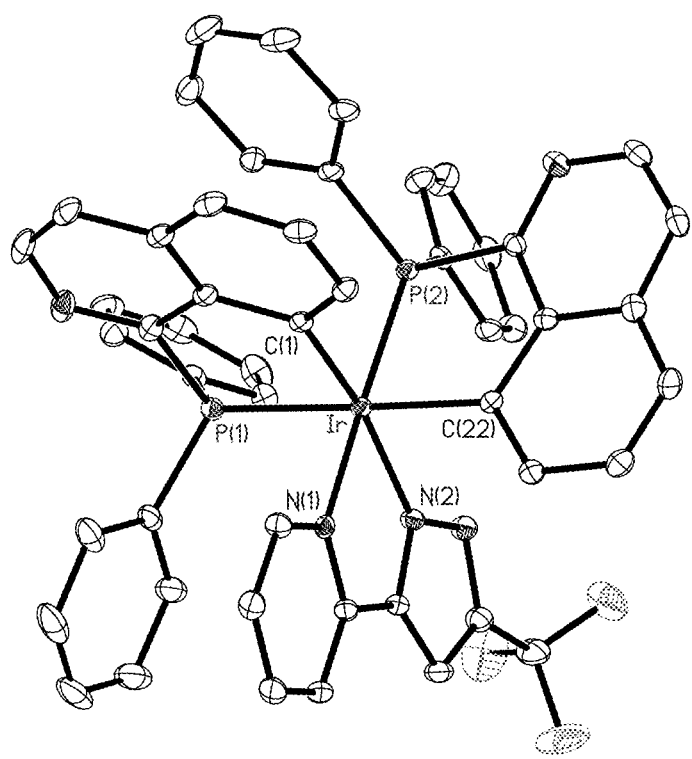
FIG. 6 shows the x-ray structure of an Ir complex (11) synthesized in Example 3 according to the present invention.

The molecular structure of [Ir(dpiq)$_2$(fppz)] (11) is shown in FIG. 6.

EXAMPLE 4

Synthesis of Ir(III) Complexes with Naphthalenyldiphenylphosphine as Carbon-Phosphorus Chelate Synthesis of [Ir(ndp)$_2$(iqbtz)] (12)

IrCl$_3$(THT)$_3$ (165 mg, 0.30 mmol), naphthalen-1-yldiphenylphosphine (ndp, 197 mg, 0.63 mmol) and sodium acetate (246 mg, 3.00 mmol) were combined in decalin (20 mL). The reaction mixture was heated to reflux for 2 h. After this had cooled to room temperature, the mixture was added 5-(1-isoquinolyl)-3-tert-butyl-1,2,4-triazaole (iqbtzH, 76 mg, 0.30 mmol) and then heated to reflux for 5 h. After cooling to room temperature and removal of solvent, the residue was loaded on a silica gel column and eluted with 1/2 ethyl acetate/hexane to give the product. The orange crystals were obtained from CH$_2$Cl$_2$ and Hexane (196 mg. 0.194 mmol, 64%).

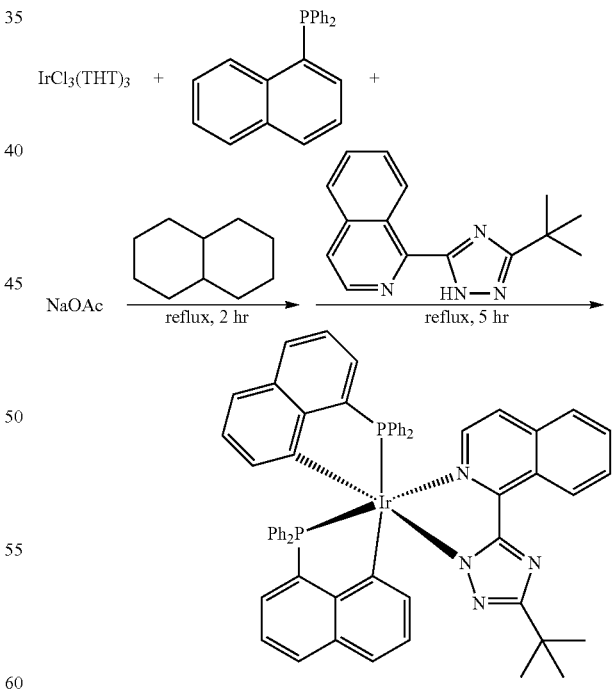

Spectral Data of (12):
MS (FAB, $^{193}$Ir): m/z 1067 (M+1)+; $^1$H NMR (500 MHz, CDCl$_3$, 294K): δ 10.10 (d, J=9.0 Hz, 1H), 8.24 (t, J=10.0 Hz, 2H), 8.11 (d, J=8.0 Hz, 1H), 8.08 (d, J=8.0 Hz, 1H), 7.78~7.84 (m, 2H), 7.54~7.62 (m, 3H), 7.46~7.52 (m, 2H), 7.32~7.40 (m, 3H), 7.29 (td, J=7.7, 2.0 Hz, 1H), 7.17~7.24

(m, 3H), 7.15 (d, J=8.0 Hz, 1H), 7.07 (dd, J=10.0, 7.0 Hz, 1H), 6.96 (t, J=6.5 Hz, 3H), 6.80 (d, J=6.5 Hz, 1H), 6.65 (t, J=8.0 Hz, 1H), 6.59 (t, J=8.0 Hz, 1H), 6.41 (d, J=7.0 Hz, 1H), 6.18~6.34 (m, 6H), 6.15 (t, J=8.5 Hz, 2H), 5.83 (t, J=8.5 Hz, 2H), 1.49 (s, 9H). $^{31}$P-{$^{1}$H} NMR (202 MHz, CDCl$_3$, 294K): δ 16.04 (d, J=12.4 Hz, 1P), 15.58 (d, J=12.4 Hz, 1P).

The photophysical properties of compounds (11) to (12) are listed in Table 3.

TABLE 3

| Sample | PL (in degassed CH$_2$Cl$_2$) | | | | |
|---|---|---|---|---|---|
| | $\lambda_{max}$ (nm) | Q.Y. | $\tau_{obs}$ (ns) | $k_r$ | $k_{nr}$ |
| (11) | 576 | 0.22 | 2 × 10$^5$ | 1.1 × 10$^3$ | 3.9 × 10$^3$ |
| (12) | 593 | 1.0 | 3.4 × 10$^5$ | 3.0 × 10$^3$ | 0 |

EXAMPLE 5

Synthesis of Ir(III) Complexes with 9-(Diphenylphosphino)carbazole as Carbon-Phosphorus Chelate Synthesis of dpc A 2.5 M hexane solution of n-BuLi (4 mL, 10.0 mmol) was added dropwise to a stirred THF solution (50 mL) of carbazole (1.67 g, 10.0 mmol) at −78° C. The reaction mixture was allowed to warm to room temperature and stirred for 2 h. The white precipitate was isolated by filtration, washed with hexane and redissolved in THF (70 mL). Chlorodiphenylphosphine (2.19 g, 9.9 mmol) was added dropwise to the solution at 0° C. The reaction mixture was allowed to warm to room temperature and stirred for 12 h. The solution was filtered and the solvent was evaporated under reduced pressure. The resulting white solid was washed with hexane and dried under vacuum to give colorless powder (2.8 g, 8.0 mmol, 80%).

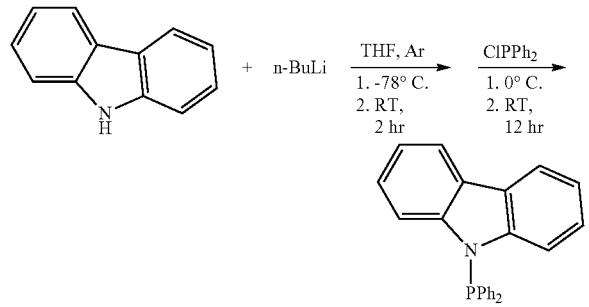

Spectral Data of dpc:

MS (EI): m/z 351 GO; $^{1}$H NMR (500 MHz, CDCl$_3$, 294K): δ 8.05~8.07 (m, 2H), 7.48~7.52 (m, 2H), 7.38~7.44 (m, 4H), 7.30~7.34 (m, 6H), 7.22~7.28 (m, 4H). $^{31}$P-{$^{1}$H} NMR (202 MHz, CDCl$_3$, 294K): δ 32.73 (s, 1P).

Synthesis of [Ir(dpc)(iqbtz)$_2$] (13)

IrCl$_3$(THT)$_3$ (165 mg, 0.30 mmol), 9-(diphenylphosphino)carbazole (dpc, 105 mg, 0.30 mmol) were combined in decalin (10 mL). The reaction mixture was heated to reflux for 2.5 h. After this had cooled to room temperature, the mixture was added sodium acetate (246 mg, 3.00 mmol) and 5-(1-isoquinolyl)-3-tert-butyl-1,2,4-triazaole (iqbtzH, 151 mg, 0.60 mmol) and then heated to reflux for 6 h. After cooling to room temperature and removal of solvent, the residue was loaded on a silica gel column and eluted with 1/2 ethyl acetate/hexane to give the product. The orange crystals were obtained from CH$_2$Cl$_2$ and hexane (50 mg. 0.048 mmol, 16%).

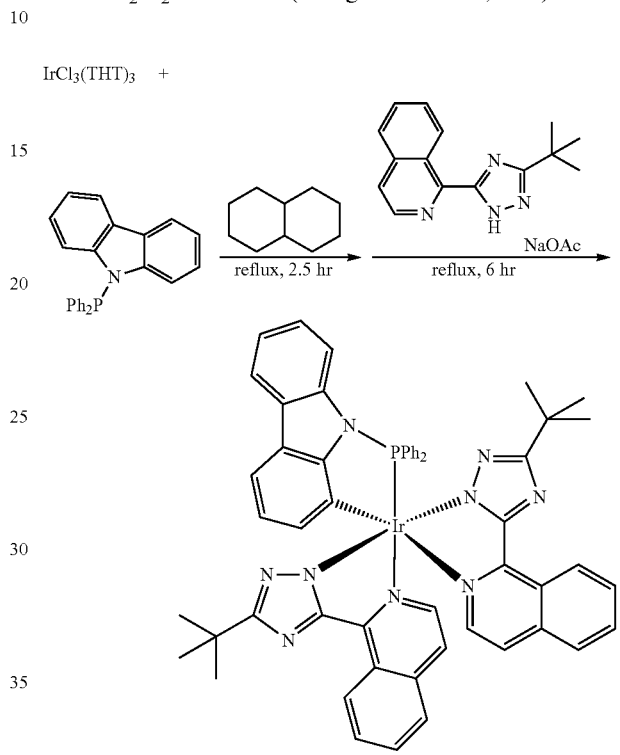

Spectral Data of (13):

MS (FAB, $^{193}$Ir): m/z 1045 (M+1)$^+$; $^{1}$H NMR (500 MHz, CDCl$_3$, 294K): δ 10.29 (d, J=8.0 Hz, 1H), 10.00 (d, J=9.0 Hz, 1H), 8.02~8.08 (m, 3H), 7.71~7.80 (m, 3H), 7.60~7.67 (m, 4H), 7.53 (d, J=6.5 Hz, 1H), 7.40~7.50 (m, 3H), 7.28 (t, J=7.5 Hz, 1H), 7.20~7.25 (m, 1H), 7.14~7.18 (m, 2H), 7.06 (d, J=7.0 Hz, 1H), 7.00 (d, J=8.0 Hz, 1H), 6.82 (t, J=8.0 Hz, 1H), 6.38~6.53 (m, 5H), 6.03 (d, J=7.0 Hz, 1H), 1.28 (s, 9H), 1.05 (s, 9H). $^{31}$P-{$^{1}$H} NMR (202 MHz, CDCl$_3$, 294K): δ 44.77 (s, 1P).

Synthesis of [Ir(dpc)$_2$(iqbtz)] (14)

IrCl$_3$(THT)$_3$ (165 mg, 0.30 mmol), 9-(diphenylphosphino)carbazole (dpc, 210 mg, 0.60 mmol) and sodium acetate (246 mg, 3.00 mmol) were combined in decalin (10 mL). The reaction mixture was heated to reflux for 2.5 h. After this had cooled to room temperature, the mixture was added 5-(1-isoquinolyl)-3-tert-butyl-1,2,4-triazaole (iqbtzH, 76 mg, 0.30 mmol) and then heated to reflux for 12 h. After cooling to room temperature and removal of solvent, the residue was loaded on a silica gel column and eluted with 1/2 ethyl acetate/hexane to give the product. The orange crystals were obtained from CH$_2$Cl$_2$ and MeOH (131 mg. 0.11 mmol, 38%).

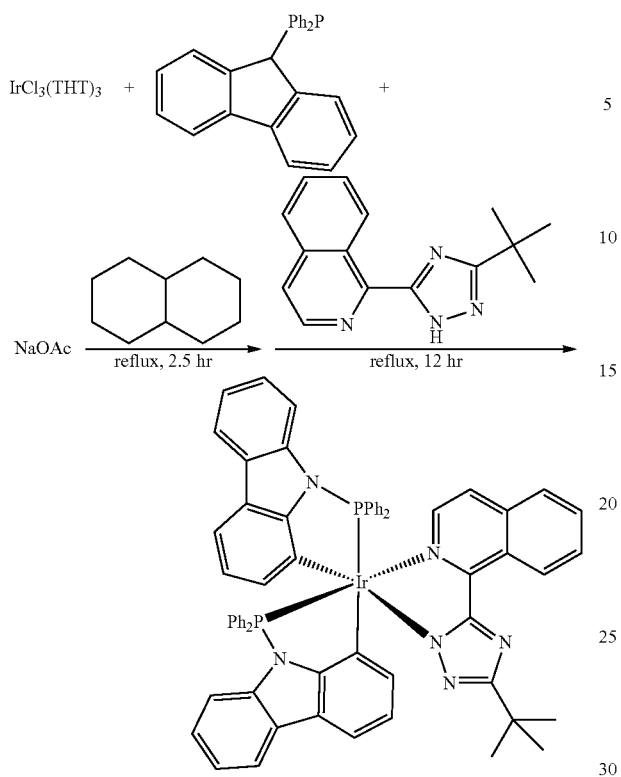

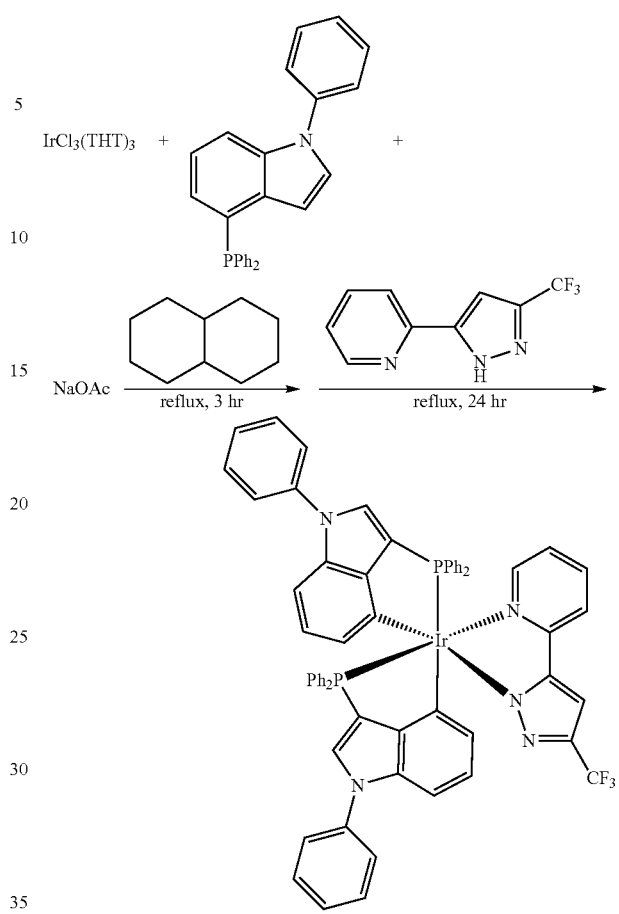

Spectral Data of (14):

MS (FAB, $^{193}$Ir): m/z 1044 (M$^+$); $^1$H NMR (500 MHz, CDCl$_3$, 294K): δ 10.03 (d, J=8.0 Hz, 1H), 8.04 (t, J=10.0 Hz, 2H), 7.96 (d, J=8.0 Hz, 1H), 7.92 (d, J=8.0 Hz, 1H), 7.82 (t, J=10.0 Hz, 2H), 7.54~7.64 (m, 4H), 7.39~7.42 (m, 2H), 7.35 (d, J=7.5 Hz, 1H), 7.29 (d, J=7.5 Hz, 1H), 7.19~7.25 (m, 3H), 7.08~7.13 (m, 2H), 7.03~7.07 (m, 3H), 6.95 (d, J=6.0 Hz, 1H), 6.87 (t, J=8.0 Hz, 1H), 6.75~6.82 (m, 2H), 6.50~6.60 (m, 3H), 6.36~6.43 (m, 3H), 6.28~6.35 (m, 4H), 5.93~6.00 (m, 3H), 1.48 (s, 9H). $^{31}$P-{$^1$H} NMR (202 MHz, CDCl$_3$, 294K): δ 48.40 (d, J=4.7 Hz, 1P), 46.42 (d, J=4.7 Hz, 1P).

EXAMPLE 6

Complexes with 4-(Diphenylphosphino)-1-phenyl-1H-indole as Carbon-Phosphorus Chelate Synthesis of [Ir(dpppi)$_2$(fppz)] (15)

IrCl$_3$(THT)$_3$ (165 mg, 0.30 mmol), 4-(diphenylphosphino)-1-phenyl-1H-indole (dpppi, 250 mg, 0.74 mmol) and sodium acetate (246 mg, 3.00 mmol) were combined in decalin (10 mL). The reaction mixture was heated to reflux for 3 h. After this had cooled to room temperature, the mixture was added 3-trifluoromethyl-5-(2-pyridyl)pyrazole (fppzH, 64 mg, 0.30 mmol) and then heated to reflux for 24 h. After cooling to room temperature and removal of solvent, the residue was loaded on a silica gel column and eluted with 1/3 ethyl acetate/hexane to give the product. The orange crystals were obtained from CH$_2$Cl$_2$ and MeOH (22 mg. 0.021 mmol, 7%).

Spectra data of (15):

MS (FAB, $^{193}$Ir): m/z 1058 (M$^+$); $^1$H NMR (CDCl$_3$, 400 MHz, 294K): δ 8.27 (d, J=7.6 Hz, 1H), 8.24 (d, J=7.6 Hz, 1H), 7.94~7.99 (m, 3H), 7.52 (dd, J=8.0, 2.8 Hz, 1H), 7.46~7.49 (m, 1H), 7.33~7.40 (m, 8H), 7.22~7.28 (m, 5H), 7.08~7.20 (m, 6H), 7.03 (td, J=7.7, 1.6 Hz, 2H), 6.69~6.86 (m, 2H), 6.71 (t, J=6.8 Hz, 1H), 6.65 (s, 1H), 6.62 (td, J=7.6, 2.0 Hz, 2H), 6.56 (t, J=6.6 Hz, 1H), 6.47~6.51 (m, 2H), 6.42 (td, J=7.6, 2.4 Hz, 2H), 6.07 (m, 2H), 5.94 (s, 1H), 5.89 (s, 1H). $^{19}$F-{$^1$H} NMR (CDCl$_3$, 470 MHz, 294K): δ −60.56 (s, 3F). $^{31}$P-{$^1$H} NMR (CDCl$_3$, 202 MHz, 294K): δ 21.88 (d, J=11.1 Hz, 1P), 10.82 (d, J=11.1 Hz, 1P).

EXAMPLE 7

General Method of Producing OLEDs

Synthesized compounds according to this disclosed specification were subject to purification by temperature-gradient sublimation in high vacuum before use in subsequent device studies. OLEDs were fabricated on the ITO-coated glass substrates with multiple organic layers sandwiched between the transparent bottom indium-tin-oxide (ITO) anode and the top metal cathode. The material layers were deposited by vacuum evaporation in a vacuum chamber with a base pressure of <10$^{-6}$ torr. The deposition system permits the fabrication of the complete device structure in a single vacuum pump-down without breaking vacuum. The deposition rate of organic layers was kept at ~0.2 nm/s. The active area of the device is 2×2 mm$^2$, as defined by the shadow mask for cathode deposition.

A device structure and materials used were ITO/NPD (30 nm)/TCTA (20 nm)/CzSi (3 nm)/CzSi: (4) 7.0 wt. % (35 nm)/UGH2: (4) 7.0 wt. % (3 nm)/UGH2 (2 nm)/BCP (50 nm)/Cs₂CO₃ (2 nm)/Ag. The α-naphthylphenylbiphenyl diamine (α-NPD) and 4,4',4''-tri(N-carbazolyl)triphenylamine (TCTA) were used as the hole-transport layer (HTL). The thin CzSi (30 Å) was served both as the hole-transport layer and as the buffer layer for blocking the high-energy triplet excitons (on (4)) from migrating to TCTA (with a lower triplet energy). Double emitting layers (CzSi and UGH2 doped with 7.0 wt. % of (4)) were used to achieve better balance between hole and electron injection/transport and thus to move the exciton formation zone away from the quenching interfaces with carrier-transport layers, taking advantage of the hole-transport nature of CzSi and the electron-transport nature of UGH2. The thin UGH2 (20 Å) was served both as the electron-transport/hole-blocking layer and as the buffer layer for blocking the high-energy triplet excitons from migrating to BCP (with a lower triplet energy). Finally, 2,9-dimethyl-4,7-diphenyl-1,10-phenanthroline (BCP) was used as the electron-transport layer, and Ag or Cs₂CO₃ were used as the electron-injection layer.

Figure 7:
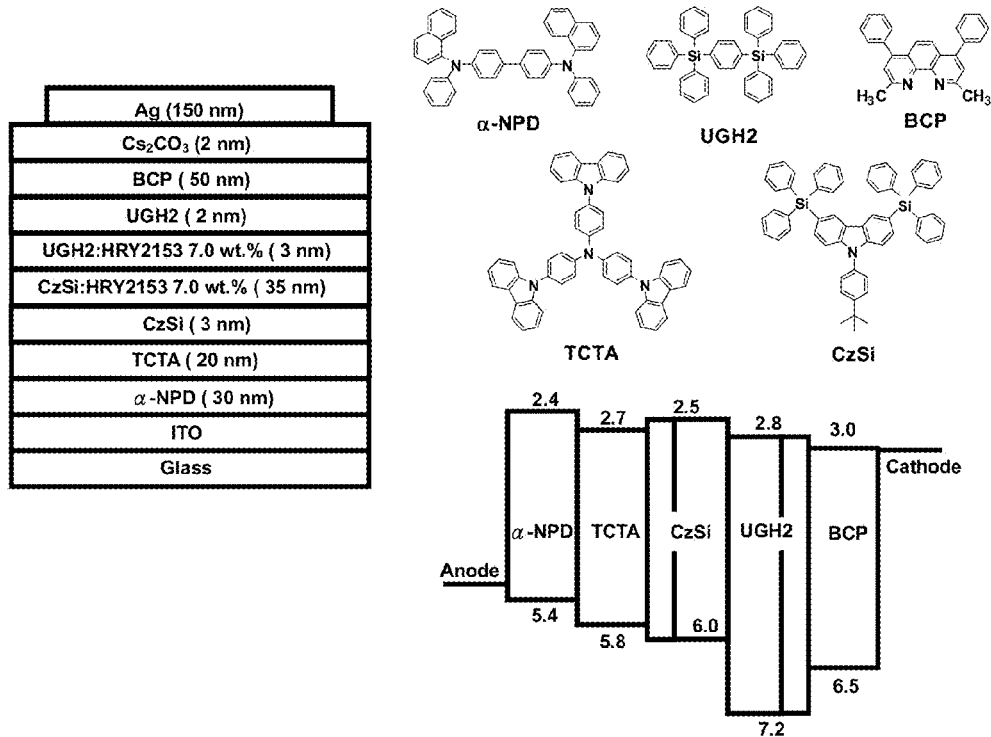
FIG. 7 shows the structure of the blue-emitting OLED made in Example 7 of the present invention and the structures of the compounds used together with an energy level diagram.

FIG. 7 shows the structure of the blue-emitting OLEDs made in this example and the structures of the compounds used together with an energy level diagram.

Figure 8:
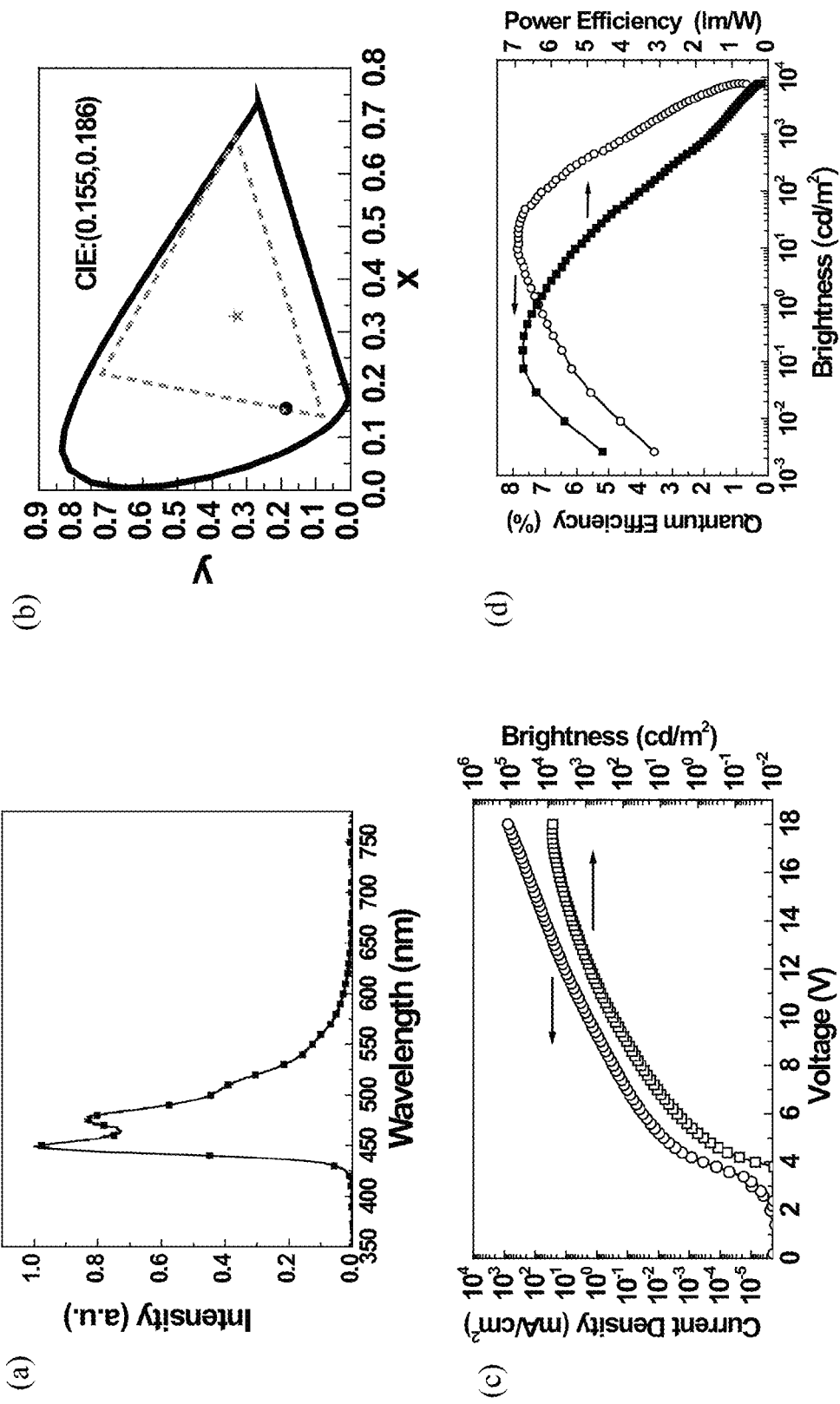
FIG. 8 show the performance of the OLED fabricated in Example 7 of the present invention, wherein (a) is EL spectrum; (b) CIE chromaticity coordinate; (c) is I-V-L characteristics, and (d) is external quantum efficiency and power efficiency versus brightness thereof.

The current-voltage-brightness (I-V-L) characterization of the light-emitting devices was performed with a source-measurement unit (SMU) and a calibrated Si photodiode with Photo Research PR650. EL spectra of devices were collected by a calibrated CCD spectrograph. The performance of the OLEDs fabricated in this example are shown FIG. 8 and Table 4.

TABLE 4

| Sample | External Quantum Efficiency (%) | Luminance Efficiency (cd/A) | Power Efficiency (lm/W) | CIE coordinate (x, y) (@ 100 cd/m²) |
|---|---|---|---|---|
| (4) Peak | 7.86 | 11.55 | 6.8 | (0.155, 0.186) |
| 100 cd/m² | 7.11 | 10.46 | 3.6 | |

The invention claimed is:

1. A phosphorescent tris-chelated transition metal complex comprising one nitrogen-nitrogen (N^N) chelate forming a coordination sphere thereof with a transition metal, and two identical carbon-phosphorus (C^P) chelates being incorporated into the coordination sphere, wherein the transition metal is iridium, platinum, osmium or ruthenium.

2. The complex of claim 1, wherein the metal is iridium.

3. The complex of claim 2, wherein the complex is represented by the Formula Id or their stereo isomers:

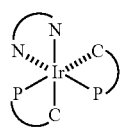

Id wherein the N and N linked with an arch have a formula of Ar¹—Ar², wherein Ar¹ is aromatic ring or a N-heterocyclic ring, and Ar² is N-heterocyclic ring, wherein N in the formula Id is a nitrogen atom contained in the heterocyclic rings of Ar₁ and Ar²; the carbon-phosphorus (C^P) chelates are presented by the P and C linked with an arch, and have a formula of Ar³—(C(R⁴R⁵))ₘ—P(Ar⁴Ar⁵), wherein m is 0, 1 or 2; Ar⁴ and Ar⁵ independently are phenyl, functionalized phenyl, iso-propyl or tert-butyl; R⁴ and R⁵ independently are H or methyl; —Ar³ is

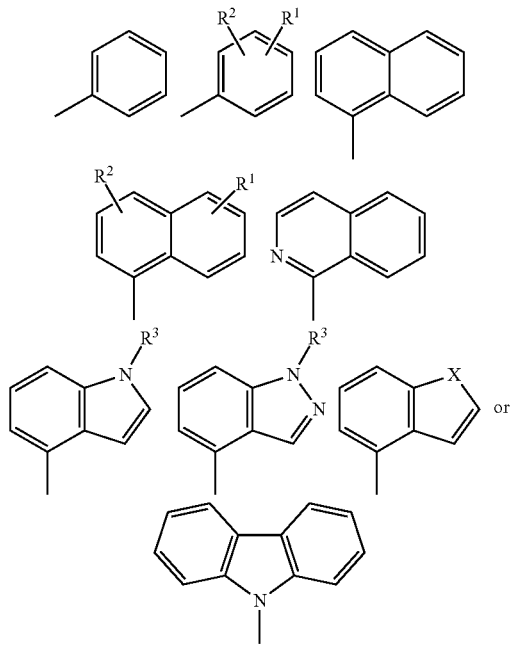

wherein R¹ and R² independently are alkyl, cyano, F or $C_nF_{2n+1}$, n is an integer of 1-3; R³ is methyl, phenyl, alkyl, cyano, and functionalized aromatic group; and X is oxygen or sulfur.

4. The complex of claim 3, wherein the carbon-phosphorus (C^P) chelates are

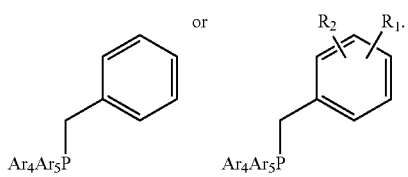

5. The complex of claim 4, wherein Ar⁴ and Ar⁵ are both phenyl, and R¹ and R² are both F.

6. The complex of claim 3, wherein the carbon-phosphorus (C^P) chelates are

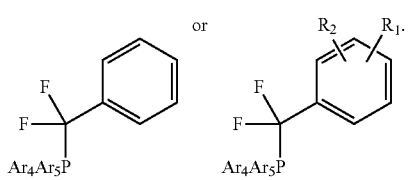

7. The complex of claim 6, wherein Ar⁴ and Ar⁵ are both phenyl, and R¹ and R² are both F.

8. The complex of claim 3, wherein the carbon-phosphorus (C^P) chelates are

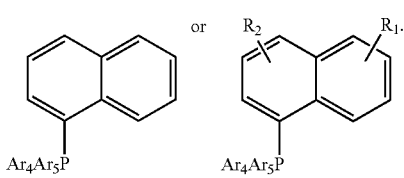

9. The complex of claim 8, wherein $Ar^4$ and $Ar^5$ are both phenyl, and $R^1$ and $R^2$ are both F.

10. The complex of claim 3, wherein the carbon-phosphorus (C^P) chelates are

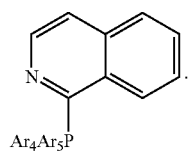

11. The complex of claim 10, wherein $Ar^4$ and $Ar^5$ are both phenyl.

12. The complex of claim 10, wherein the nitrogen atom is relocated to other position except at the 8-position.

13. The complex of claim 3, wherein the carbon-phosphorus (C^P) chelates are

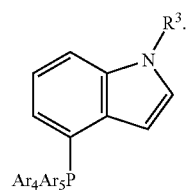

14. The complex of claim 13, wherein $Ar^4$, $Ar^5$ and $R^3$ are all phenyl.

15. The complex of claim 3, wherein the carbon-phosphorus (C^P) chelates are

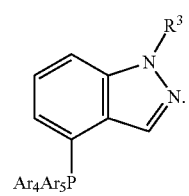

16. The complex of claim 15, wherein $Ar^4$, $Ar^5$ and $R^3$ are all phenyl.

17. The complex of claim 3, wherein the carbon-phosphorus (C^P) chelates are

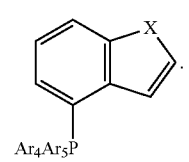

18. The complex of claim 17, wherein $Ar^4$ and $Ar^5$ are phenyl.

19. The complex of claim 3, wherein the carbon-phosphorus (C^P) chelates are

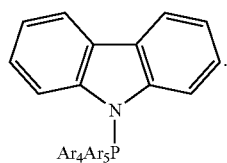

20. The complex of claim 19, wherein $Ar^4$ and $Ar^5$ are phenyl.

21. The complex of claim 3, wherein the nitrogen-nitrogen (N^N) chelates are

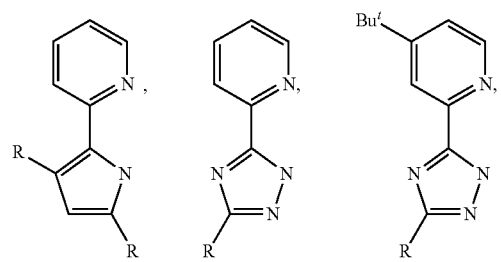

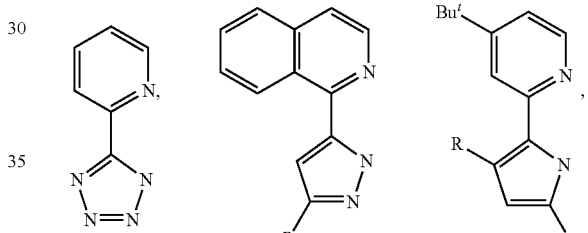

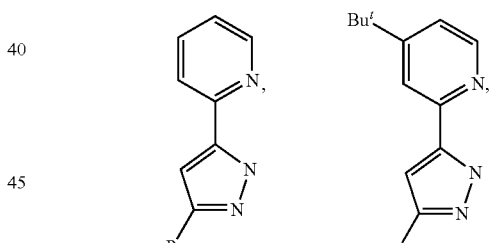

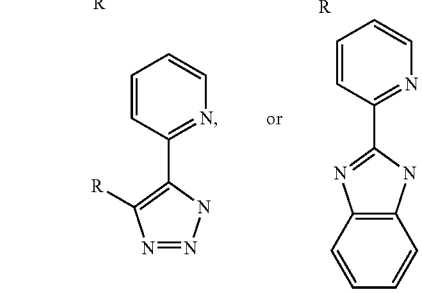

wherein R is $CF_3$, tert-butyl, phenyl or functionalized phenyl group, and $Bu^t$ is tert-butyl.

* * * * *